United States Patent [19]

Muchowski et al.

[11] 3,931,282

[45] Jan. 6, 1976

[54] 11α-HYDROXYMETHYL PROSTAGLANDINS

[75] Inventors: Joseph M. Muchowski; Angel Guzman, both of Mexico City, Mexico

[73] Assignee: Syntex (U.S.A.) Inc., Palo Alto, Calif.

[22] Filed: Feb. 21, 1974

[21] Appl. No.: 444,689

[52] U.S. Cl. ..... 260/468 D; 260/293.05; 260/345.8; 260/445 R; 260/445.8 R; 260/488 R; 260/501.1; 260/501.11; 260/501.17; 260/514 D; 424/305; 424/317
[51] Int. Cl.$^2$ ................... C07C 61/38; C07C 69/74
[58] Field of Search ......... 260/468 D, 514 D, 514 A

[56] References Cited
UNITED STATES PATENTS 3,845,042  10/1974  Strike et al. ...................... 260/240

FOREIGN PATENTS OR APPLICATIONS

| 2,313,868 | 10/1973 | Germany | 260/468 |
|---|---|---|---|
| 804,342 | 2/1974 | Belgium | 260/468 |
| 7,311,403 | 2/1974 | Netherlands | 260/468 |
| 813,988 | 10/1974 | Belgium | 260/468 |

Primary Examiner—Robert Gerstl
Attorney, Agent, or Firm—Gerard A. Blaufarb; William B. Walker

[57] ABSTRACT

Novel process for the preparation of 11α-hydroxymethyl derivatives of natural (8R-) and racemic 9-keto-15α-hydroxy- and 9,15α-dihydroxy-prosta-5-cis,13-trans-dienoic and prost-13-transenoic acids, and the novel 15-methyl and ethyl substituted derivatives thereof, as well as the esters of the primary and secondary hydroxy groups and the non-toxic, pharmaceutically acceptable salts of the novel compounds.

15 Claims, No Drawings

11α-HYDROXYMETHYL PROSTAGLANDINS

The present invention realtes to a novel process for preparing certain prostanoic acid derivatives and to certain novel compounds obtained thereby.

More particularly, this invention relates to a novel process for preparing 11α-hydroxymethyl derivatives of 9-keto-15α-hydroxy- and 9ξ,15α-dihydroxyprosta-5-cis,13-trans-dienoic acids as well as the 13-monounsaturated derivatives thereof, and to the novel 15-methyl or ethyl substituted derivatives of such compounds. Also included are certain esters of the primary and secondary hydroxyl groups, and the pharmaceutically acceptable, non-toxic esters and salts of the carboxylic acid function of these novel compounds.

Prostaglandins are members of a relatively new class of hormonal agents with a remarkable range of biological and pharmaceutical properties. These compounds belong to a group of chemically related 20-carbon chain hydroxy fatty acids having the basic skeleton of prostanoic acid:

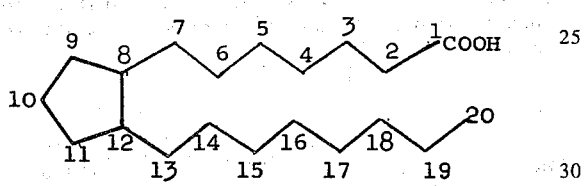

For a review on prostaglandins and the definition of primary prostaglandins, see for example S. Bergström, *Recent Progress in Hormone Research*, 22, pp. 153–175 (1966) and *Science*, 157, page 382 (1967) by the same author.

Prostaglandins are widely distributed in mammalian tissues and have been isolated from natural sources in very small amounts. In addition, a number of the naturally occurring prostaglandins have been prepared by chemical synthesis; note for example, E. J. Corey et al., *J. Am. Chem. Soc.*, 91, page 5675 (1969), *J. Am. Chem. Soc.* 92, page 2586 (1970) and *J. Am. Chem. Soc.*, 93, pages 1489–1493 (1971) and references cited therein, W. P. Schneider et al., *J. Am. Chem. Soc.*, 90, page 5895 (1968), U. Axen et al., *Chem. Commun.*, page 303 (1969) and W. P. Schneider, *Chem. Commun.*, page 304 (1969).

It has also been reported by A. J. Weinheimer et al., [*Tetrahedron Letters*, 5183 (1969)] that a type of coral, the sea whip or sea fan *Plexaura homomalla* found in reefs off the Florida coast, in the Caribbean region, contains high concentrations of prostaglandin derivatives of the PGA$_2$ series, to which they assigned the unnatural (R) configuration for the hydroxyl group at C-15. More recently, W. P. Schneider et al., [*J. Am. Chem. Soc.*, 94, 2122 (1972)] reported that some forms of *P. homomalla* contain, instead of the (15R)-prostaglandins, free or esterified derivatives of (15S)-PGA$_2$, identical with the prostaglandins derived from mammalian sources. They also found that some specimens of this gorgonian may contain both (15R) and (15S) prostaglandins.

Because of the remarkable range of biological and pharmacological properties exhibited by this family of compounds, a great deal of interest has focused upon such compounds, and the preparation of analogs of such compounds; accordingly, we have discovered a novel process for preparing 11α-hydroxymethyl prostaglandins and certain novel 15-alkyl derivatives thereof.

The novel prostaglandin derivatives of the present invention can be represented by the following formula:

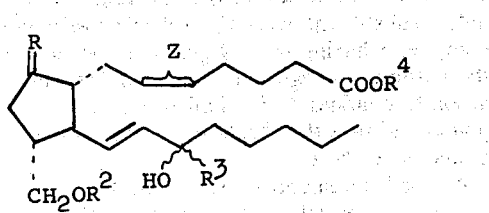

wherein
R is a keto group or the grouping

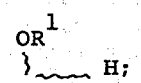

each of $R^1$ and $R^2$ is hydrogen or an acyl group of 1 to 6 carbon atoms;
$R^3$ is methyl or ethyl;
$R^4$ is hydrogen, a lower alkyl group of 1 to 6 carbon atoms or the pharmaceutically acceptable, non-toxic salts of compounds in which $R^4$ is hydrogen;
Z is a saturated linkage or a cis double bond and the wavy lines ( ξ ) indicate the α or β configuration or mixtures thereof, provided that when $R^3$ is α, the hydroxyl group, attached to the same carbon atom as $R^3$, is β; and when $R^3$ is β, the hydroxyl group, attached to the same carbon atom as $R^3$ is α.

The dotted lines shown in the above formula and in the formulas below indicate that the substituents are in α configuration, i.e., below the plane of the cyclopentane ring.

The double bonds in the compounds of the present invention have the same configuration as in natural prostaglandins of the PGE$_1$, PGE$_2$, PGF$_{1\alpha}$ and PGF$_{2\alpha}$ series, i.e., the double bond at C-5,6 is in cis-configuration and the double bond at C-13,14 is in trans-configuration.

These novel compounds possess asymmetric centers and thus can be produced as racemic mixtures. The racemic mixtures can be resolved if desired, at appropriate stages by methods known to those skilled in the art, to obtain the respective individual antimers. It is to be understood that the individual antimers as well as mixtures of both antimers are encompassed within the scope of the present invention. The preferred antimeric compounds are the 8R-antimers, i.e., the optically active forms corresponding to prostaglandins obtained from natural sources.

When the compounds of the present invention are racemic mixtures, they are produced starting from racemates, while when the compounds of the invention are individual antimers, they are preferably obtained starting from the appropriate individual antimer.

For the sake of simplicity only one antimer of each pair will be depicted in the description of the process and Claims; however, it is to be understood that the mirror images for the racemic mixtures and the individual antimers are also encompassed thereby.

The use of the symbol R preceding a substituent designates the absolute stereochemistry of that substituent according to the Cahn-Ingold-Prelog rules [see Cahn et al., *Angew. Chem. Inter, Edit.*, Vol., 5, p. 385

(1966), errata p. 511; Cahn et al., *Angew. Chem.*, Vol. 78, p. 413 (1966); Cahn and Ingold, *J. Chem. Soc.*, (London), 1951, p. 612; Cahn et al., *Experientia*, Vol. 12, p. 81 (1956); Cahn., *J. Chem. Educ.*, Vol. 41, p. 116 (1964)]. Because of the interrelation of the designated substituent with the other substituents in the compound having α or β prefixes, the designation of the absolute configuration of one substituent fixes the absolute configuration of all substituents in the compound and thus the absolute configuration of the compound as a whole.

As used hereinabove and below the term "conventionally hydrolyzable esters" refers to those physiologically acceptable ester groups employed in the pharmaceutical art. The conventionally hydrolyzable esters of the primary and secondary hydroxyl groups of the compounds of the present invention are derived from hydrocarbon carboxylic acids containing from 1 to 6 carbon atoms or from a substituted hydrocarbon carboxylic acid having from 1 to 6 carbon atoms, wherein the substituent is selected from the group consisting of hydroxy, alkoxy containing up to 6 carbon atoms, hydrocarbon carboxylic acyloxy groups containing up to 6 carbon atoms, nitro, amino or halogen. Typical conventional hydrolyzable esters thus included within the scope of the term and the instant invention are formate, acetate, propionate butyrate, valerate, caproate, diethylacetate, trimethylacetate, t-butylacetate, acetoxyacetate, trichloroacetate, β-chloropropionate, aminoacetate, diethylaminoacetate and the like.

The conventionally hydrolyzable esters of the carboxylic acid function are derived from hydrocarbons containing from 1 to 6 carbon atoms, particularly the methyl, ethyl and propyl esters.

The addition salts of the compounds of the present invention are derived from pharmaceutically acceptable basic salts, including metal salts such as sodium, potassium, calcium, magnesium, aluminum and the like, as well as organic amine salts such as ammonium, triethylamine, 2-dimethylaminoethanol, 2-diethylaminoethanol, lysine, arginine, caffeine, procaine, N-ethylpiperidine, hydrabramine and the like.

The term "pharmaceutically acceptable" refers to esters and salts which do not significantly adversely affect the properties of the parent compound.

The novel process for producing 11α-hydroxymethyl prostaglandin derivatives (without a methyl or ethyl substituent at C-15) can be illustrated by the following sequence of reactions:

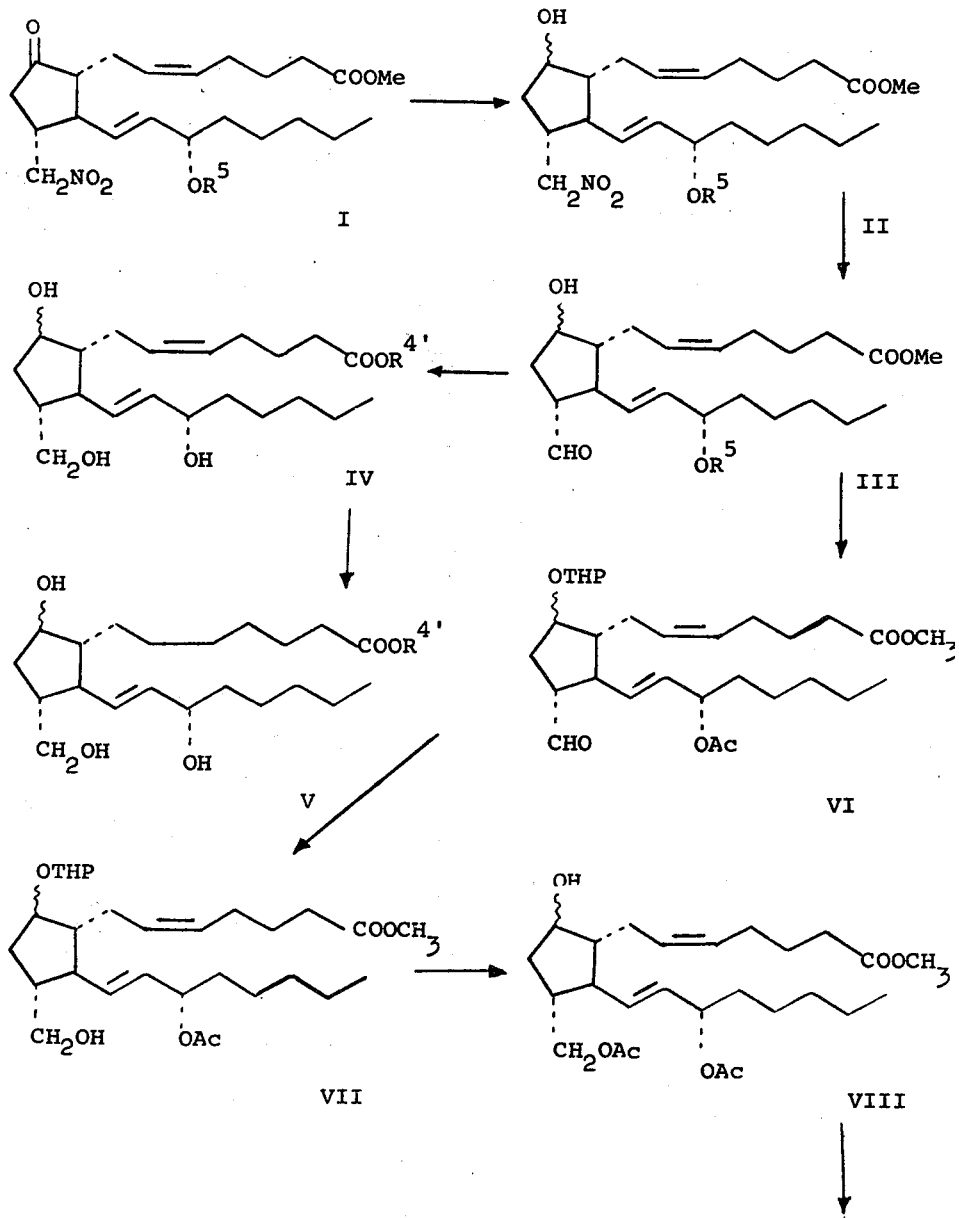

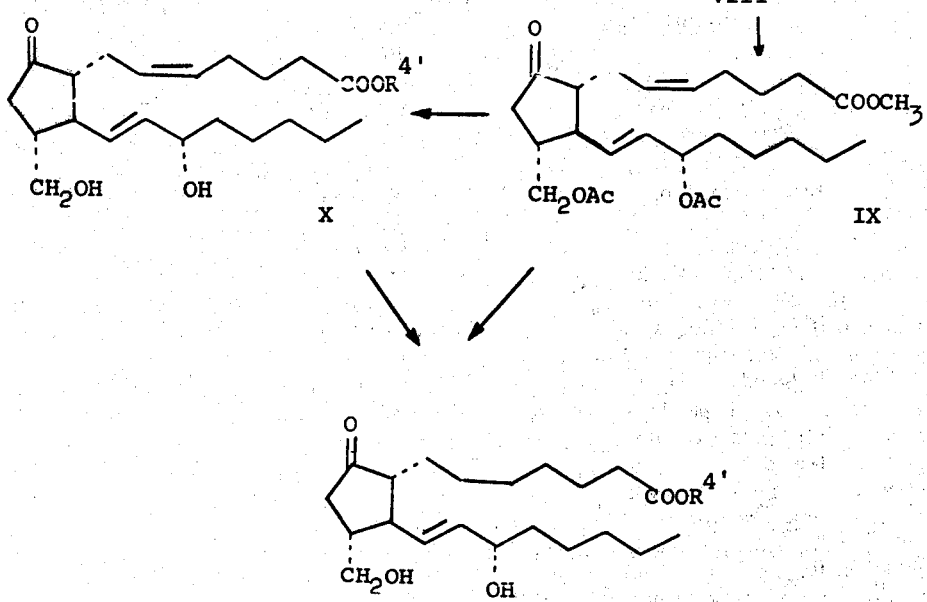

wherein

R⁴′ is hydrogen or methyl;

R⁵ is hydrogen or acetyl;

Ac is acetyl and THP is tetrahydropyranyl.

In practicing the process outlined above, 8R-9-keto-11α-nitromethyl-15α-hydroxyprosta-5-cis,13-trans-dienoic acid methyl ester, the racemic compound or the 15-acetylated derivatives thereof (compounds of formula I), are reduced with sodium borohydride in methanol solution, at about 0°C for a period of time of the order of 1 to several hours, preferably for about 1 to 2 hours, using equimolecular amounts of the reagent and starting material to give a mixture of the corresponding 9α- and 9β-hydroxylated derivatives of formula II, the 9β-hydroxy isomer predominating. The individual isomers are separated by chromatographic techniques, preferably by chromatography on Florisil; the 9α-hydroxy isomer is less polar than the 9β-hydroxy compound.

The nitromethyl group in compounds of formula II is converted into a formyl group via formation of a nitronic salt followed by reaction with titanium trichloride in a buffered medium, to yield the corresponding 11α-formyl compounds of formula III.

Typically, a nitromethyl compound of the formula II is treated with about 1.1 molar equivalents of sodium methoxide in anhydrous methanol under an inert atmosphere, i.e., under nitrogen or argon atmosphere, for a short period of time, of the order of 5 to 15 minutes, to form the nitronic salt, which upon reaction with 6 to 10 molar equivalents of titanium trichloride, using a 20% aqueous solution of titanium trichloride in the presence of an excess of ammonium acetate as buffer, at about room temperature for a period of time of the order of 30 minutes to 2 hours, produces the 11α-formyl derivative of formula III. In the preferred embodiments, there are used 8 molar equivalents of titanium trichloride per molar equivalent of the nitromethyl compound and about 25 parts of ammonium acetate, a period of about 1 hour being generally sufficient to complete the reaction. The product is isolated from the reaction mixture by conventional techniques, such as dilution with water, extraction with a solvent immiscible with water, evaporation of the solvent and chromatographic purification of the residue.

The aldehyde compounds of formula III, (R⁵=H) are then submitted to a second reduction with sodium borohydride, to yield the desired hydroxymethyl compounds of formula IV (R⁴′ = Me). This reaction is also effected at about 0°C as described with regard to the reduction of the 9-keto group (I → II), for a period of time of the order of 30 minutes to 2 hours.

Upon selective reduction of the C-5,6-double bond in the 11α-hydroxymethyl compounds of formula IV (R⁴′ = Me) there are produced the monounsaturated compounds of formula V (R⁴′ = Me). This selective reduction can be effected by the procedure described by Koch et al., in *Journal of Labelled Compounds*, Vol. VI, No. 4, page 395 (October–December 1970) using tris(triphenylphosphine) chlororhodium as catalyst, in a suitable inert organic solvent or mixture of solvents, such as a benzene-acetone mixture, at about room temperature, or using a palladium-charcoal catalyst in a lower aliphatic alcohol as solvent, i.e., in methanol, or ethanol solution at a temperature comprised between −20°C to room temperature, until absorption of about one molar equivalent of hydrogen, using in both cases a thin layer chromatographic analytical technique to follow the progress of the reaction.

The methyl ester compounds of formulas IV and V (R⁴′ = Me) can be converted into the corresponding free acids (R⁴′ = H) by alkaline treatment, preferably by reaction with an excess of an alkali metal carbonate in aqueous methanol, under an inert atmosphere, i.e., under nitrogen or argon atmosphere, for a period of time of about 12 to 20 hours at room temperature or under slight heating, followed by acidification.

By conventional reaction of the racemic or 8R-antimeric aldehyde of formula III ($R^5$ = acetyl) with dihydropyran in the presence of an acid catalyst, e.g., p-toluenesulfonic acid in an inert organic solvent such as methylene chloride there is obtained the corresponding 9-tetrahydropyranyloxy-11α-formyl-15-acetoxy compound of formula VI, whose formyl group is reduced with sodium borohydride in methanol solution, to yield the 11α-hydroxymethyl derivative of formula VII. The latter compound is then esterified with acetic anhydride in pyridine solution, in a conventional manner, and the diacetate thus obtained is in turn treated with aqueous acetic acid, using particularly 65% aqueous acetic acid, to hydrolyze the tetrahydropyranyloxy function at C-9, thus producing the corresponding 9-hydroxylated compound of formula VIII. This hydrolysis is conducted at room temperature for a period of time of about 12 to 20 hours, preferably for about 15 hours, optionally in the presence of an ethereal solvent miscible with water, e.g., tetrahydrofuran, dimethoxyethane and the like.

Upon oxidation of compounds of formula VIII with chromium trioxide, using particularly an 8N solution of chromic acid in acetone (Jones' reagent), there is produced the 9-keto prostadienoic acid compound of formula IX. This reaction is effected at low temperature of the order of −20° to 0°C, for a period of time of about 15 minutes to 1 hour. In the preferred embodiments the reaction is conducted at about −10°C for about 30 minutes. The 9-keto compounds of formula IX are then hydrolyzed with a mild base to yield the methyl ester of the 8R-antimeric or racemic prostadienoic acid of formula X ($R^{4\,\prime}$ = Me) or the corresponding free acids (X, $R^{4\,\prime}$ = H) depending upon the conditions used.

Thus, by treatment of a compound of formula IX with two equivalents of an anhydrous alkali metal carbonate such as sodium carbonate or potassium carbonate in a dry lower aliphatic alcohol, particularly methanol, at about room temperature or below for a period of time of between 2 to 4 hours, preferably for about 3 hours, at about 22°C, the reaction time depending upon the temperature at which the hydrolysis takes place, produces the selective hydrolysis of the acetoxy functions, thus yielding 8R-9-keto-11α-hydroxymethyl-15α-hydroxy-prosta-5-cis,13-trans-dienoic acid methyl ester or the racemic compound (X, $R^{4\,\prime}$ = Me). Upon reaction of the latter compounds with an excess of an alkali metal carbonate, such as those previously mentioned, in aqueous methanol at room temperature, or under slight heating, i.e., at a temperature of the order of 20° to 40°C for a period of time of about 12 to 20 hours, preferably for about 16 hours, the carboxylic acid ester is hydrolyzed, thus yielding, after acidification, the free acid (X, $R^{4\,\prime}$ = H). Both hydrolysis steps are preferably conducted under an inert atmosphere, i.e., under nitrogen or argon atmosphere.

Alternatively, the hydrolysis of both the acetoxy functions and the carboxylate function can be effected in a single step following the second procedure, i.e., using aqueous conditions and an excess of the alkali metal carbonate, however, better yields and a product of a higher purity is obtained when the hydrolysis is effected by the two step sequence.

By selective hydrogenation of the C-5,6 double bond in compounds of formula X ($R^{4\,\prime}$ = Me) in the presence of tris(triphenylphosphine) chlorohodium or a palladium charcoal catalyst, as described hereinabove with regard to the transformation of compounds of formula IV into compounds of formula V there are produced the racemic or 8R-antimeric monounsaturated 9-keto prostaglandin derivatives of formula XI ($R^4$ = Me) which are converted into the corresponding free acids (XI, $R^{4\,\prime}$ = H) by reaction with an alkali metal carbonate in aqueous methanol.

Alternatively, the double bond at C-5,6 can be hydrogenated into the diacetoxy compounds of formula IX and thereafter hydrolyzing the acetoxy functions and the methyl ester group, as previously mentioned for the prostadienoic acid derivatives of the invention.

The novel 15-methyl and 15-ethyl substituted 11α-hydroxymethyl prostaglandin derivatives of the present invention can be obtained as illustrated by the following sequence of reactions:

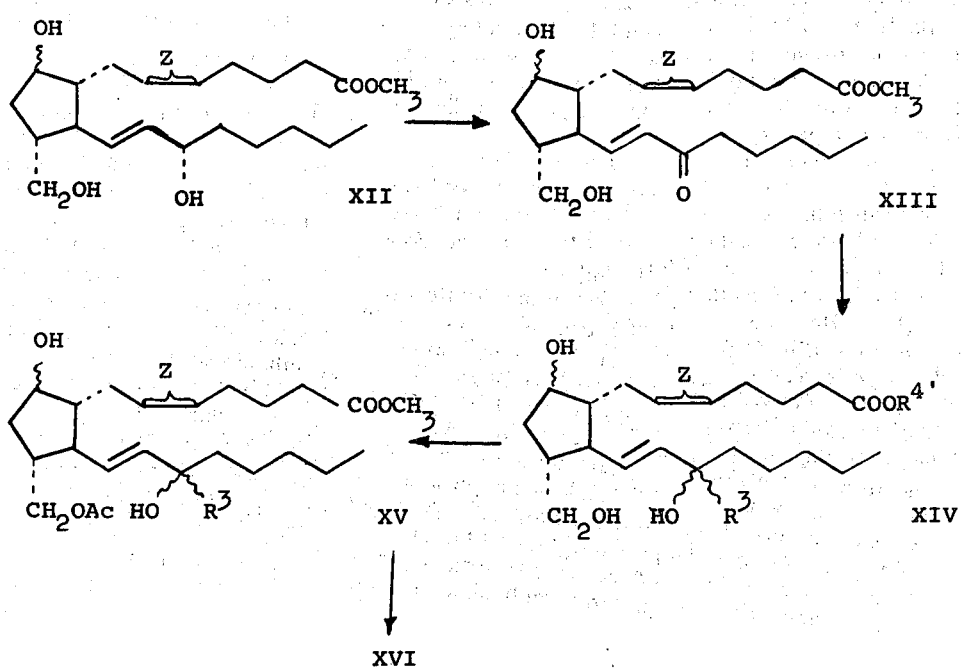

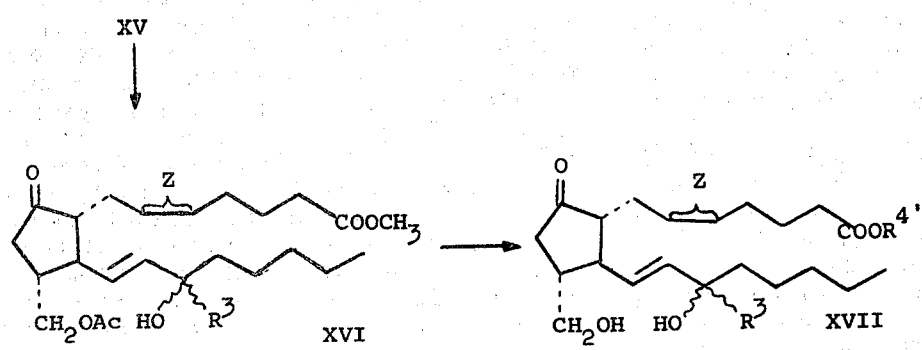

wherein $R^3$, $R^{4'}$, Ac and Z have the above-indicated meaning.

In practicing the processes illustrated above, a racemic or 8R-antimeric compound of formula XII (which is a composite of formulas IV and V, $R^{4'}$ = Me, above) is selectively oxidized at C-15 with an excess of manganese dioxide or 2,3-dichloro-5,6-dicyano-1,4-benzoquinone in a suitable inert organic solvent, e.g., chloroform, tetrahydrofuran, dioxane and the like to produce the corresponding 15-keto derivative of formula XIII. When manganese dioxide is used as reagent, the reaction is conducted at room temperature, for a period of time of 18 to 40 hours, under vigorous stirring, using preferably chloroform or tetrahydrofuran as solvent. The oxidizing agent is added portionwise, at 4–6 hours intervals. When the oxidation is effected using 2,3-dichloro-5,6-dicyano-1,4-benzoquinone as reagent, the reaction is preferably conducted at a temperature above room temperature, i.e., at about 50° to 60°C, using particularly dioxane or benzene as solvents, for a period of time of the order of 14 to 20 hours, preferably for about 18 hours.

In any case, the course of the reaction can be followed by thin layer chromatography or by periodic determination of the ultraviolet spectrum. When the reaction is complete, the product is isolated from the reaction mixture by conventional techniques, such as separation of the insoluble material by filtration, evaporation of the filtrate and purification of the residue by chromatographic techniques.

Treatment of the 15-keto compounds of formula XIII with an excess of an anlkylmagnesium halide, i.e., methyl or ethylmagnesium bromides or chlorides, yields the coresponding 15 ξ -alkyl-15 ξ -hydroxy compounds of formula XIV ($R^3$ = Me, Et, $R^{4'}$ = Me), as mixtures of the respective 15α-hydroxy-15β-alkyl- and 15β-hydroxy-15α-alkyl isomers. This reaction is preferably carried out in ether or tetrahydrofuran solution, using from 6 to 18 molar equivalents of the Grignard reagent per molar equivalent of starting compound, at a temperature of between −25°C to room temperature, for a period of time of 1 to 4 hours, under an inert atmosphere.

Typically, the reaction is conducted by adding the Grignard reagent, portionwise, to a previously cooled solution (−20°C) of compound XIII in diethylether or tetrahydrofuran, under argon or nitrogen atmosphere. The temperature of the reaction mixture is then allowed to rise to about −5°C, an additional amount of the Grignard reagent is added, following the course of the reaction by thin layer chromatographic techniques, the reaction being generally complete within about 2 hours.

Alternatively, the reaction can be carried out using a molar excess of an alkyllithium as reagent, i.e., methyl-, or ethyllithium, conducting the reaction at about −70° to −20°C for a short period of time of the order of 10 to 30 minutes, however, a more selective alkylation is obtained when using a Grignard reagent.

The mixture of 15α-hydroxy-15β-alkyl- and 15β-hydroxy-15α-alkyl compounds of formula XIV is separated into the individual isomers by thin layer chromatography.

In an alternative process, the hydroxyl groups in compounds of formula XIII can be protected as the silyloxy derivatives, particularly as the trimethylsilylethers prior to the reaction with the alkylating agent, by following procedures known in the art, see for example Pierce "Silylation of Organic compounds", Pierce Chemical Co., Rockford, Ill. (1968). Conveniently, this reaction can be done by using a mixture of hexamethyldisilazane and trimethylchlorosilane or with N-trimethylsilyldiethylamine in acetone as esterifying agents, hydrolyzing the protective groups with aqueous methanol in the presence of a trace of acid or tetrabutylammonium fluoride once the alkyl substituent at C-15 has been introduced.

The hydroxymethyl group in compounds of formula XIV ($R^{4'}$ = Me) is then selectively esterified with acetic anhydride in pyridine, to produce the acetoxymethyl derivatives of formula XV. This selective esterification is effected using about 1.1 molar equivalents of acetic anhydride in pyridine solution, conducting the reaction at low temperature, i.e., at about 0°–5°C for about 1 to 4 hours.

The 11α-acetoxymethyl compounds of formula XV are then oxidized with chromium trioxide under alkaline conditions, to yield the corresponding 9-keto derivatives of formula XVI. Suitable oxidizing agent are, for example, chromium trioxide-pyridine complex, chromium trioxide-dipyridine complex (Collins' reagent) and dicyclohexylcarbodiimide or diisopropylcarbodiimide in dimethyl sulfoxide (Moffat's reagent), using particularly chromium trioxide-dipyridine complex, conducting the reaction at low temperature, in the range of −10° to 0°C, for a short period of time of the order of 5 to 20 minutes.

The acetoxymethyl function in compounds of formula XVI is then selectively saponified with anhydrous potassium carbonate, using about one equivalent of this reagent, at room temperature for about 1 to 2 hours, thus yielding the corresponding racemic or 8R-antimeric methyl ester compounds of formula XVII, R⁴ ′ = Me.

The methyl ester compounds of formulas XIV and XVII (R⁴ ′ = Me) are converted into the respective free prost-13-trans-enoic and prosta-5-cis,13-trans-dienoic acids of the invention (XIV and XVII,R⁴ ′ = H) by chemical or enzymatic hydrolysis methods.

When the hydrolysis is effected chemically, the reaction is effected with potassium carbonate in aqueous methanol, for a period of time of about 12 to 24 hours, preferably for about 16 hours, at room temperature and under nitrogen or argon atmosphere, followed by careful acidification with a weak acid, such as acetic acid, at low temperature, i.e., at about 0° to −10°C, to avoid dehydration of the tertiary hydroxyl group at C-15.

In the preferred embodiments, the hydrolysis of the methyl ester group is effected enzymatically.

Typically, this enzymatic reaction is conducted in aqueous solutions, using particularly a crude pancreatic lipase commercially available (Sigma Steapsin), however, other enzyme systems which are known as useful for the hydrolysis of compounds unstable to alkaline or acid conditions can also be practical, e.g., other lipases obtainable from bacterial sources, such as the partially purified lipase obtained from *Corynebacterium acnes* culture supernatant, or a lipase of those that are known to act on water insoluble esters of long chain fatty acids [L. Sarda et al., *Biochem. Biophys. Acta.* 23, 264 (1957)], or baker's yeast [C. J. Sih et al., *J. C. S. Chem. Comm.* 240 (1972)], or with the enzymes contained in the gorgonian *Plexaura homomalla* (Esper).

The enzymatic hydrolysis with a crude pancreatic lipase can be conducted in a buffered aqueous solution containing sodium chloride and calcium chloride, at a neutral or almost neutral pH, at a temperature of between 22° to 30°C, preferably at about 25° to 27°C, adjusting the pH of the reaction mixture to 7.2 to 7.4 by addition of, for example dilute sodium hydroxide solution, at intervals. The starting alkyl ester compound is dissolved in the previously prepared buffered lipase aqueous solution by sonication at about 37°C using from about 0.5 ml. to about 1 ml. of the lipase solution per milligram of substrate. The methyl ester group is readily hydrolyzed within a short period of time, of the order of 5 minutes to 1 hour. The course of the reaction can be followed by thin layer chromatography; when the hydrolysis is complete, the free acid can be isolated from the reaction mixture by conventional techniques, such as acidification with a dilute acid solution, e.g., using dilute acetic acid, extraction with a solvent immiscible with water, e.g., diethyl ether, ethyl acetate, methylene chloride and the like, evaporation of the solvent and purification of the crude product by chromatographic techniques.

The hydrolysis with the enzymes contained in the residue of the gorgonian *Plexaura homomalla* (after extraction of its prostaglandin content) is conducted in the same aqueous saline solution used in the case of the hydrolysis with the crude pancreatic lipase, employing from about 5 to about 20 parts by weight of finely ground recently extracted gorgonian residue per one part of the alkyl ester to be hydrolyzed, stirring the reaction mixture at a temperature of between 20° to 37°C, preferably at about room temperature, for a period of time of the order of 16 to 24 hours, at a pH of 7.5–7.7. When the hydrolysis is complete, as demonstrated by thin layer chromatographic analysis, the reaction mixture is diluted with acetone, carefully acidified and the insoluble material separated by filtration. The product is isolated from the filtrate by concentration to a small volume, extraction, evaporation and chromatographic purification, as described hereinbefore.

The above-described enzymatic hydrolysis methods are also applicable for the hydrolysis of the methyl ester compounds of formulas IV, V, X and XI, (R⁴ ′ = Me), above.

Alternatively, the 9-keto-11α-hydroxymethyl compounds of formula XVII can be prepared by the method illustrated as follows:

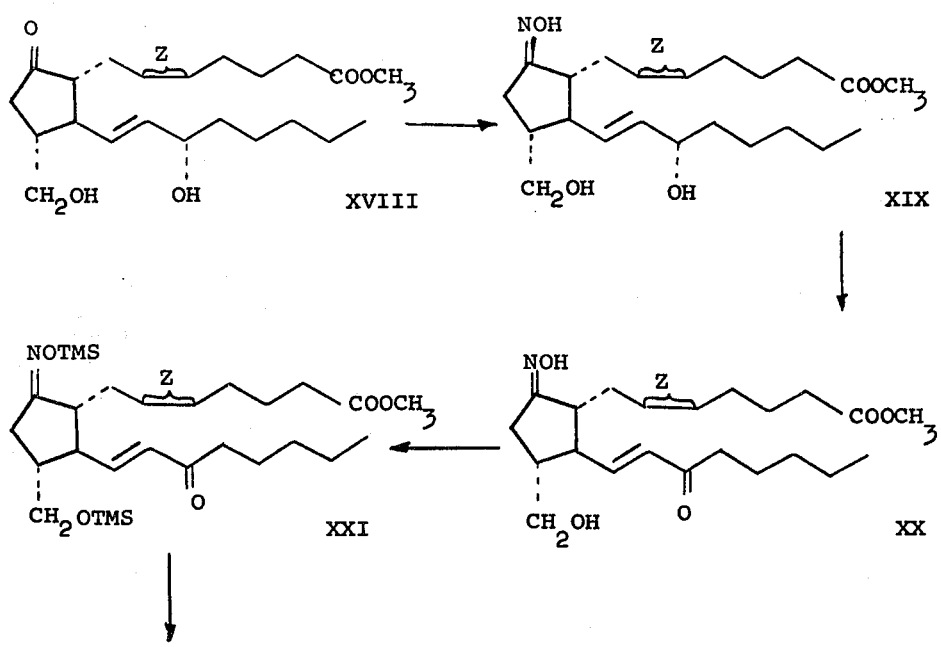

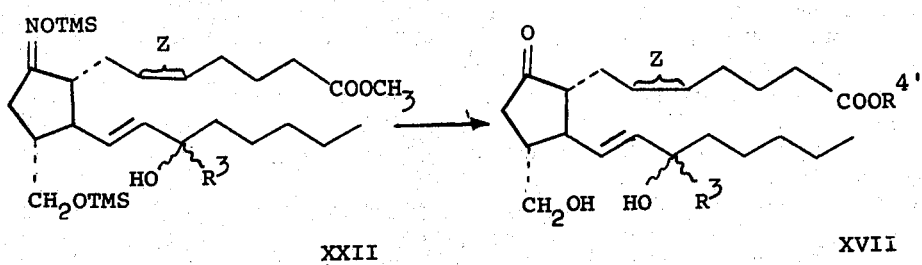

XXII → XVII wherein $R^3$, $R^{4'}$ and Z have the above indicated meaning and TMS is trimethylsilyl [Si(CH$_3$)$_3$].

In practicing the process outlined above, a racemic or 8R-antimeric compound of formula XVIII (composite of formulas X and XI, $R^{4'}$ = Me, above) is converted into the corresponding oxime of formula XIX by conventional procedures, e.g., by reaction with hydroxylamine hydrochloride in aqueous methanol, at room temperature for a period of time of the order of 16 to 24 hours. The oxime of formula XIX is then oxidized with manganese dioxide or 2,3-dichloro-5,6-dicyano-1,4-benzoquinone, as described hereinabove in detail for the obtention of compounds of formula XIII, to produce the corresponding 15-keto compounds of formula XX.

By reaction of a compound of formula XX with a silylating agent, using particularly a mixture of hexamethyldisilazane and trimethylchlorosilane or N-trimethylsilyldiethylamine as reagent there is produced the corresponding trimethylsilyloxy derivative represented by formula XXI, which upon treatment with a Grignard reagent or with methyl- or ethyllithium, as previously described in detail for the transformation of compounds of formula XIII into XIV produces a mixture of the corresponding 15 ξ -alkyl-15 ξ -hydroxy derivatives represented by formula XXII.

The mixture of 15α-hydroxy-15β-alkyl and 15β-hydroxy-15α-alkyl compounds thus obtained is separated into the individual isomers by thin layer chromatography (previous hydrolysis of the trimethylsilyloxy groups with aqueous methanol in the presence of a trace of acid) and thereafter the oxime is hydrolyzed to regenerate the 9-keto function, thus producing the separated racemic or 8R-antimeric 9-keto-15α-hydroxy-15β-alkyl and 9-keto-15β-hydroxy-15α-alkyl prostenoic and prostadienoic acid ester compounds of formula XVII ($R^{4'}$ = Me). The deoximation reaction is effected under mild conditions, for example by the methods described by E. J. Corey et al., in *J. Am. Chem. Soc.*, 92, 5276 (1970) or A. McKillop et al., *J. Am. Chem. Soc.*, 93, 4918 (1971) and references cited therein.

The first method involves the conversion of the oxime into the O-acetate derivative followed by reaction with an excess, using at least 2 molar equivalents, of chromous acetate in 90% aqueous tetrahydrofuran, at a temperature of the order of 25° to 65°C. for about 10 to 24 hours.

The second method comprises treatment of the oxime with thallium (III) nitrate, using about 1 to 1.1 molar equivalents of the reagent per mol of starting compound. The reaction is conducted at room temperature or below for a short period of time, of the order of 5 to 30 minutes, in an inert organic solvent, followed by filtration of the thallium (I) nitrate with precipitates, and brief treatment of the filtrate with dilute acid to decompose the intermediate nitroso compound. In accordance with our invention, this reaction is conducted in methanol solution, at about 20°C. using aqueous acetic acid to decompose the nitroso intermediate.

Hydrolysis of the oxime can also be effected using titanium trichloride as described by Timms and Wilsmith, *Tetrahedron Letters*, 195 (1971).

Alternatively, the hydrolysis of the oxime can be effected on the mixture of the 15α and 15β-hydroxy isomers, separating the individual isomers afterwards, by thin layer chromatography.

The alkyl ester group is then hydrolyzed by chemical or enzymatic methods, as previously mentioned.

The hydroxymethyl group at C-11 as well as the secondary hydroxyl group at C-9 in the novel compounds of the present invention can be esterified in a conventional manner, i.e., by reaction with the appropriate carboxylic acid anhydride or chloride in pyridine solution, to produce the corresponding mono-, or diesters, depending upon the particular prostaglandin derivative.

The alkyl esters of the carboxylic acid function in the novel compounds of the present invention, other than the methyl esters can be prepared by treatment of the free acid with an excess of, for example, diazoethane or diazopropane in ether or methylene chloride solution, in a conventional manner, or by reaction with the desired lower alkyl iodide in the presence of lithium carbonate, at room temperature.

The salt derivatives of the novel 11α-hydroxymethyl-15 ξ -methyl and 11α-hydroxymethyl-15 ξ -ethyl prostaglandin derivatives hereof can be prepared by treating the corresponding free acids with about one molar equivalent of a pharmaceutically acceptable base per molar equivalent of free acid.

Suitable pharmaceutically acceptable bases include, for example, sodium hydroxide, potassium hydroxide, magnesium hydroxide, calcium hydroxide, ammonium hydroxide, trimethylamine, triethylamine, tripropylamine, 2-dimethylaminoethanol, 2-diethylaminoethanol, arginine, lysine, caffeine, procaine, hydrabamine and the like. Typically, the reaction is conducted in an aqueous solution, alone or in combination with an inert, water miscible organic solvent, at a temperature of about from 0° to 30°C, preferably at room temperature. Typical inert, water miscible organic solvents include methanol, ethanol, isopropanol, butanol, dioxane or tetrahydrofuran. When divalent metal salts are prepared such as the calcium salts or magnesium salts, the free acid starting material is treated with at least one half molar equivalent of the pharmaceutically acceptable base.

In conducting the above-described processes, it is generally preferred to separate or isolate the respective products of each reaction step prior to their use as starting materials in subsequent steps. Illustrative non-limiting separation and isolation procedures can be had by reference to the appropriate Examples set forth hereinbelow. Also, although the above processes have been described with regard to methyl ester compounds as starting materials the carboxylic acid function can also be protected as the ethyl or propyl esters, particularly when starting from racemic compouunds obtained by total synthesis.

The compounds of formula I used as starting materials in the process of the present invention are known compounds, or can be obtained by the method illustrated by the following equation:

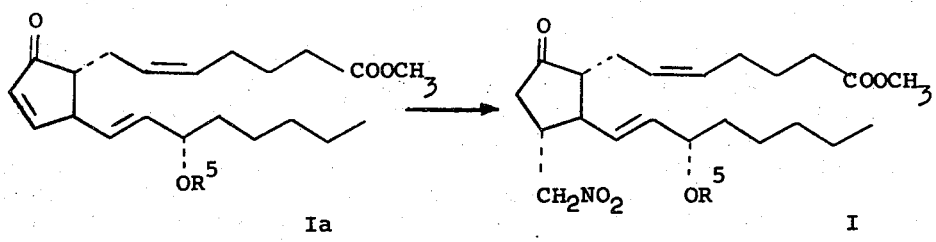

wherein $R^5$ has the above-indicated meaning.

This process comprises the reaction of natural $PGA_2$ methyl ester, or the corresponding acetate, isolated from the gorgonian Plexaura homomalla (see W. P. Schneider et al, *J. Am. Chem. Soc.* 94, 2122 (1972) or the racemic compounds thereof (compounds represented by formula Ia) with nitromethane in the presence of Triton B, as described by C. V. Grudzinskas et al., in Tetrahedron Letters No. 2, 141 (1973) to yield the respective nitromethyl derivative of formula I. The racemic compounds of formula Ia are in turn obtained from racemic $PGE_2$, described by E. J. Corey et al, *J. Am. Chem. Soc.* 91, 5675 (1969) by dehydration with 90% aqueous acetic acid, in accordance with the method of J. E. Pike et al., *J. O. C.* 34, 3552 (1969) followed by conventional esterification of the carboxylic acid function with ethereal diazomethane and optional acylation of the 15-hydroxy group.

The compounds, esters and salts of the invention exhibit prostaglandin-like biological activities and thus are useful in the treatment of mammals where the use of prostaglandins is indicated. The compounds, esters and salts of the invention are bronchodilators and thus are useful in treating mammals for bronchial spasm or wherever strong bronchodilators are indicated. These compounds are also useful in controlling or palliating hypertension in mammals and further exhibit central nervous system depressant activity in mammals, and are useful as sedatives. In addition, the compounds are useful for inducing labor, in pregnancy, and for inducing menses to correct or reduce menstrual abnormalities.

The compounds and/or salts of the invention, can be administered in a wide variety of dosage forms, either alone or in combination with other pharmaceutically compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid or aerosol, in which the compound and/or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the compounds and/or salts can, for example, be administered as an aerosol comprising the compounds or salts in an inert propellant together with a cosolvent (e.g., ethanol) together with optional preservatives and buffering agents. Additional general information concerning the inhalation administration of aerosols can be had by reference to U.S. Pat. Nos. 2,868,691 and 3,095,355.

The compounds of this invention are typically administered in dosages of about from 0.01 to 10 mg. per Kg. of body weight. The precise dosage will, of course, vary depending upon the mode of administration, condition being treated and host.

The following Preparations and Examples illustrate the invention, but are not intended to limit its scope. When using 8R-antimeric compounds as starting materials 8R-antimeric compounds are obtained as products, while starting from racemic compounds the products obtained are racemates. The abbreviation t.l.c. refers to thin-layer chromatography and all mixture ratios used with regard to liquids refer to volume ratios. Also, where necessary, examples are repeated to provide sufficiente starting materials for subsequent examples.

PREPARATION 1

To a solution of 10 g. of 8R-9-keto-15α-hydroxyprosta-5-cis,10,13-trans-trienoic acid methyl ester [natural $PGA_2$ methyl ester, isolated from the gorgonian *Plexaura homomalla* (Esper) and purified by successive chromatographies, first on a Florisil column using increasing percentages of ether in methylene chloride and thereafter by thin layer chromatography on silica gel, using methylene chloride-ethyl acetate as gradient] in 10 ml. of tetrahydrofuran is added 20 ml. of nitromethane, and to the resulting stirred mixture is added dropwise, at room temperature and under argon atmosphere, 10 ml. of a 40% methanolic solution of trimethylbenzylammonium hydroxide (Triton B). The reaction mixture is stirred at room temperature for 22 hours and then poured into 200 ml. of water, acidified with acetic acid and extracted three times with ethyl acetate. The combined organic extracts are washed with saturated sodium bicarbonate solution, and saturated sodium chloride solution, dried over sodium sulfate and evaporated to dryness under reduced pressure. The oily residue is purified by t.l.c. using hexane-ethyl acetate (1:1) as gradient thus producing the pure 8R-9-keto-11α-nitromethyl-15α-hydroxyprosta-5-cis,13-trans-dienoic acid methyl ester as main product, and a small amount of 8R-9-keto-14-nitromethyl-15α-hydroxyprosta-5-cis,13-trans-dienoic acid methyl ester.

In a similar manner, starting from 8R-9-keto-15α-acetoxyprosta-5-cis,10,13-trans-trienoic acid methyl ester, also isolated from the gorgonian Plexaura homomalla, there is obtained 8R-9-keto-11α-nitromethyl-15α-acetoxyprosta-5-cis, 13-trans-dienoic acid methyl ester as main product.

PREPARATION 2

A mixture of 850 mg. of 9-keto-11α,15α-dihydroxyprosta-5-cis,13-trans-dienoic acid [obtained as described by E. J. Corey et al. in *J. Am. Chem. Soc.* 91, 5675 (1969)] and 30 ml. of 90% aqueous acetic acid is stirred at 60°C, under an atmosphere of argon, for 18 hours. The solvent is then eliminated under reduced pressure at a temperature not higher than 20°C. The oily residue is dissolved in 10 ml. of methylene chloride and treated with an excess of an ethereal solution of diazomethane, maintaining the reaction mixture at room temperature for 10 minutes. The solvents and excess reagent are eliminated by vacuum distillation, and the residue is purified by t.l.c. to afford the pure 9-keto-15α-hydroxyprosta-5-cis,10,13-trans-trienoic acid methyl ester.

Upon reaction of the foregoing compound with nitromethane in the presence of Triton B, in accordance with the method of Preparation 1, there is obtained 9-keto-11α-nitromethyl-15α-hydroxyprosta-5-cis,13-trans-dienoic acid methyl ester.

The latter compound is then esterified with acetic anhydride in pyridine solution, 1 hour at room temperature, thus yielding 9-keto-11α-nitromethyl-15α-acetoxyprosta-5-cis,13-trans-dienoic acid methyl ester.

EXAMPLE 1

To a solution of 500 mg. of 8R-9-keto-11α-nitromethyl-15α-hydroxyprosta-5-cis,13-trans-dienoic acid methyl ester in 5 ml. of methanol, cooled to 0°C is added 47.5 mg. of sodium borohydride, and the reaction mixture is stirred at 0°C for 2 hours. It is then poured into water and extracted with ethyl acetate. The combined organic extracts are washed with 50% saturated sodium chloride solution, dried over sodium sulfate and evaporated to dryness under reduced pressure. The oily residue is dissolved in methylene chloride and purified by chromatography on Florisil. Those fractions eluted with methylene chloride-methanol (98:2) afford the pure, separated isomers, 8R-11α-nitromethyl-9α,15α-dihydroxyprosta-5-cis,13-trans-dienoic acid methyl ester and 8R-11α-nitromethyl-9β,15α-dihydroxyprosta-5-cis,13-trans-dienoic acid methyl ester (8R-antimers of II, $R^5$ =H), in a 1:3 ratio, the 9α-hydroxy isomer being less polar than the 9β-hydroxy compound.

By the same method 9-keto-11α-nitromethyl-15α-hydroxyprosta-5-cis,13-trans-dienoic acid methyl ester is converted into 11α-nitromethyl-9α,15α-dihydroxyprosta-5-cis, 13-trans-dienoic acid methyl ester and 11α-nitromethyl-9β,15α-dihydroxyprosta-5-cis,13-trans-dienoic acid methyl ester, the 9β-hydroxy isomer predominating.

EXAMPLE 2

To a solution of 207 mg. of 8R-11α-nitromethyl-9β,15α-dihydroxyprosta-5-cis,13-trans-dienoic acid methyl ester in 2 ml. of anhydrous methanol is added a recently prepared solution of sodium methoxide (obtained from 15 mg. of sodium and 3 ml. of anhydrous methanol) under argon atmosphere. The reaction mixture is stirred at room temperature for 10 minutes and then poured into an aqueous solution containing 5 g. of ammonium acetate, 6 ml. of water and 6 ml. of 20% aqueous titanium trichloride solution. The resulting mixture is stirred at room temperature, under argon atmosphere, for 1 hour and then diluted with 100 ml. of ice-water. The product is extracted carefully (4 × 50 ml) with ethyl acetate and the combined organic extracts washed with sodium chloride solution to neutral, dried over sodium sulfate and evaporated to dryness under reduced pressure, thus yielding 8R-11α-formyl-9β,15α-dihydroxyprosta-5-cis,13-trans-dienoic acid methyl ester as an oil. (8R-antimer of III, $R^5$ = H).

In a similar manner starting from 8R-11α-nitromethyl-9α,15α-dihydroxyprosta-5-cis,13-trans-dienoic acid methyl ester, there is obtained 8R-11α-formyl-9α,15α-dihydroxyprosta-5-cis,13-trans-dienoic acid methyl ester.

By the same method starting from the corresponding racemic 11α-nitromethyl compounds there are produced the respective 11α-formyl derivatives, namely, 11α-formyl-9β,15α-dihydroxyprosta-5-cis,13-trans-dienoic acid methyl ester and 11α-formyl-9α,15α-dihydroxyprosta-5-cis,13-trans-dienoic acid methyl ester.

EXAMPLE 3

To a solution of 200 mg. of 8R-11α-formyl-9β,15α-dihydroxyprosta-5-cis,13-trans-dienoic acid methyl ester in 5 ml. of methanol, cooled to 0°C is added 20 mg. of sodium borohydride, and the reaction mixture is stirred at 0°C for 90 minutes. It is then diluted with 60 ml. of ethyl acetate and washed to neutral with saturated sodium chloride solution, dried over sodium sulfate and evaporated to dryness under reduced pressure. The oily residue is purified by t.l.c. using a methylene chloride-methanol mixture (95:5) as eluant, to obtain the pure 8R-11α-hydroxymethyl-9β,15α-dihydroxyprosta-5-cis,13-trans-dienoic acid methyl ester (8R-antimer of IV, $R^{4'}$ = Me) in pure form.

By the same method but using 8R-11α-formyl-9α,1-5α-dihydroxyprosta-5-cis,13-trans-dienoic acid methyl ester, 11α-formyl-9α,15α-dihydroxyprosta-5-cis,13-trans-dienoic acid methyl ester and 11α-formyl-9β,15α-dihydroxyprosta-5-cis,13-trans-dienoic acid methyl ester, as starting materials there are respectively obtained:

8R-11α-hydroxymethyl-9α,15α-dihydroxyprosta-5-cis,13-trans-dienoic acid methyl ester, 11α-hydroxymethyl-9α,15α-dihydroxyprosta-5-cis,13-trans-dienoic acid methyl ester and 11α-hydroxymethyl-9β,15α-dihydroxyprosta-5-cis,13-transdienoic acid methyl ester.

EXAMPLE 4

A. To a solution of 750 mg. of 8R-9-keto-11α-nitromethyl-15α-acetoxyprosta-5-cis,13-trans-dienoic acid methyl ester in 10 ml. of methanol cooled to 0°C is added 100 mg. of sodium borohydride, and the reaction mixture is maintained at the same temperature for 1 hour. It is then diluted with 50 ml. of ethyl acetate and washed with 50% saturated sodium chloride solution, dried over sodium sulfate and evaporated to dryness under vacuo. The oily residue is purified by thin layer chromatography using methylene chloride-ethyl acetate (80:20) as eluant, thus obtaining the pure, separated isomers, 8R-9α-hydroxy-11α-nitromethyl-15α-acetoxyprosta-5-cis,13-trans-dienoic acid methyl ester and 8R-9β-hydroxy-11α-nitromethyl-15α-acetoxyprosta-5-cis,13-trans-dienoic acid methyl ester, in a 1:4 ratio. The 9α-isomer is less polar than the 9β-hydroxyisomer.

B. By following the method of Example 2, 220 mg. of 8R-9β-hydroxy-11α-nitromethyl-15α-acetoxyprosta-5-cis,13-trans-dienoic acid methyl ester are treated with titanium trichloride in the presence of sodium methoxide and ammonium acetate, to afford 8R-9β-hydroxy-11α-formyl-[15α-acetoxyprosta-5-cis,13-trans-dienoic acid methyl ester (8R-antimer of III, $R^5$ = Ac).

By the same method 8R-9α-hydroxy-11α-nitromethyl-15α-acetoxyprosta-5-cis,13-trans-dienoic acid methyl ester is converted into 8R-9α-hydroxy-11α-formyl-15α-acetoxyprosta-5-cis,13-trans-dienoic acid methyl ester.

By repeating this Example but using 9-keto-11α-nitromethyl-15α-acetoxyprosta-5-cis,13-trans-dienoic acid methyl ester as starting material there are obtained 9β-hydroxy-11α-formyl-15α-acetoxyprosta-5-cis,13-trans-dienoic acid methyl ester and 9α-hydroxy-11α-formyl-15α-acetoxyprosta-5-cis,13-trans-dienoic acid methyl ester as final products.

EXAMPLE 5

A solution of 2.36 g. of 8R-9β-hydroxy-11α-formyl-15α-acetoxyprosta-5-cis,13-trans-dienoic acid methyl ester in 50 ml. of anhydrous methylene chloride is treated with 4.5 ml. of freshly distilled dihydropyran and 100 mg. of p-toluenesulfonic acid, and the resulting mixture is maintained at room temperature for 18 hours. It is then poured into 50 ml. of saturated sodium bicarbonate solution, the organic layer separated and the aqueous phase extracted with methylene chloride. The combined methylene chloride extracts are washed with saturated sodium chloride solution, dried and evaporated to dryness under vacuo, thus affording 8R-9β-tetrahydropyranyloxy-11α-formyl-15α-acetoxyprosta-5-cis,13-trans-dienoic acid methyl ester (8R-antimer of VI).

In a similar manner, 8R-9α-hydroxy-11α-formyl-15α-acetoxyprosta-5-cis,13-trans-dienoic acid methyl ester is converted into the corresponding 9α-tetrahydropyranyloxy derivative.

EXAMPLE 6

A. To a solution of 405 mg. of 8R-9β-tetrahydropyranyloxy-11α-formyl-15α-acetoxyprosta-5-cis,13-trans-dienoic acid methyl ester in 5 ml. of anhydrous methanol, cooled to 0°C is added 38 mg. of sodium borohydride and the resulting mixture is stirred for 30 minutes at 0°C. It is then poured into 30 ml. of water and extracted with ethyl acetate (3 × 30 ml). The combined organic extracts are washed with sodium chloride solution to neutral, dried over sodium sulfate and evaporated to dryness under vacuo. The oily residue is purified by t.l.c. using hexane-ethyl acetate (1:1) as eluant to obtain 8R-9β-tetrahydropyranyloxy-11α-hydroxymethyl-15α-acetoxyprosta-5-cis,13-trans-dienoic acid methyl ester in pure form (8R-antimer of VII).

B. A mixture of 1.1 g. of 8R-9β-tetrahydroryranyloxy-11α-hydroxymethyl-15α-acetoxyprosta-5-cis,13-trans-dienoic acid methyl ester, 5 ml. of pyridine and 3 ml. of acetic anhydride is kept at room temperature for 1 hour at the end of which time it is evaporated to dryness under vacuo and the residue dissolved in 60 ml. of ethyl acetate. The resulting solution is washed with 1% hydrochloric acid solution, saturated sodium bicarbonate solution and water, dried and evaporated to dryness, to afford 8R-9β-tetrahydropyranyloxy-11α-acetoxymethyl-15α-acetoxyprosta-5-cis,13-trans-dienoic acid methyl ester.

C. A mixture of 1.1 g. of 8R-9β-tetrahydropyranyloxy-11α-acetoxymethyl-15α-acetoxyprosta-5-cis,13-trans-dienoic acid methyl ester, 5 ml. of dimethoxyethane and 27 ml. of 65% aqueous acetic acid is kept at room temperature for 15 hours. It is then poured into water and extracted with ethyl acetate. The combined organic extracts are washed with saturated sodium bicarbonate solution and saturated sodium chloride solution, dried over sodium sulfate and evaporated to dryness under reduced pressure, to yield 8R-9β-hydroxy-11α-acetoxymethyl-15α-acetoxyprosta-5-cis,13-trans-dienoic acid methyl ester (8R-antimer of VIII).

By repeating the procedures of this Example but using 8R-9α-tetrahydropyranyloxy-11α-formyl-15α-acetoxyprosta-5-cis,13-trans-dienoic acid methyl ester as starting material there are successively obtained:

8R-9α-tetrahydropyranyloxy-11α-hydroxymethyl-15α-acetoxyprosta-5-cis,13-trans-dienoic acid methyl ester, 8R-9α-tetrahydropyranyloxy-11α-acetoxymethyl-15α-acetoxyprosta-5-cis,13-trans-dienoic acid methyl ester and 8R-9α-hydroxy-11α-acetoxymethyl-15α-acetoxyprosta-5-cis,13-trans-dienoic acid methyl ester.

EXAMPLE 7

A solution of 510 mg. of 8R-9β-hydroxy-11α-acetoxymethyl-15α-acetoxyprosta-5-cis,13-trans-dienoic acid methyl ester in 25 ml. of purified acetone is cooled to −10°C and treated, under nitrogen atmosphere and under stirring, with 0.5 ml. of an 8N solution of chromic acid (prepared by mixing 26 g. of chromium trioxide with 23 ml. of concentrated sulfuric acid and diluting with water to 100 ml.). The reaction mixture is stirred for 30 minutes at −10°C, 0.5 ml. more of the 8N chromic acid solution is added and stirred for an additional 30 minute period at the same temperature. It is then poured into water and extracted with ethyl acetate (3 × 50 ml.) and the combined organic extracts washed with saturated sodium chloride solution, dried over sodium sulfate and evaporated to dryness under reduced pressure. The oily residue is purified by t.l.c. using hexane-ethyl acetate (1:1) as gradient, to obtain the pure 8R-9-keto-11α-acetoxymethyl-15α-acetoxyprosta-5-cis,13-trans-dienoic acid methyl ester (8R-antimer of IX).

The same compound is obtained using 8R-9α-hydroxy-11α-acetoxymethyl-15α-acetoxyprosta-5-cis,13-trans-dienoic acid methyl ester as starting material.

EXAMPLE 8

Fifty milligrams of 8R-9-keto-11α-acetoxymethyl-15α-acetoxyprosta-5-cis,13-trans-dienoic acid methyl ester are dissolved in 2 ml. of anhydrous methanol and treated with 29 mg. (2 molar equivalents) of potassium carbonate, under nitrogen atmosphere. The reaction mixture is stirred for 3 hours at room temperature, poured into water and acidified with 1% dilute hydrochloric acid and extracted with three 20 ml. portions of ethyl acetate. The combined organic extracts are washed with saturated sodium chloride solution, dried over sodium sulfate and evaporated to dryness under vacuo, thus affording 8R-9-keto-11α-hydroxymethyl-15α-hydroxyprosta-5-cis,13-trans-dienoic acid methyl ester (8R-antimer of X, $R^{4\prime}$ = Me).

EXAMPLE 9

Examples 5, 6, 7 and 8 are repeated using 9β-hydroxy-11α-formyl-15α-acetoxyprosta-5-cis,13-trans-dienoic acid methyl ester as starting material, to afford 9-keto-11α-hydroxymethyl-15α-hydroxyprosta-5-cis,13-trans-dienoic acid methyl ester as final product.

EXAMPLE 10

Ten milligrams of 8R-9-keto-11α-hydroxymethyl-15α-hydroxyprosta-5-cis,13-trans-dienoic acid methyl ester are dissolved in a mixture of 1 ml. of methanol, 1 ml. of water and 45 mg. of potassium carbonate. The reaction mixture is maintained at room temperature for 16 hours, under nitrogen atmosphere, 10 ml. of water are then added, and the reaction mixture is then evaporated under reduced pressure to half volume. It is then acidified to pH 2 with 2N hydrochloric acid and extracted several times with ethyl acetate. The combined organic extracts are dried over sodium sulfate and evaporated to dryness under reduced pressure to yield 8R-9-keto-11α-hydroxymethyl-15α-hydroxyprosta-5-cis,13-trans-dienoic acid, (8R-antimer of X, $R^{4\prime}$ = H) which can be further purified by thin layer chromatography.

Likewise, 9-keto-11α-hydroxymethyl-15α-hydroxyprosta-5-cis,13-trans-dienoic acid methyl ester is converted into the free acid.

EXAMPLE 11

Fifteen milligrams of 8R-11α-hydroxymethyl-9β,15α-dihydroxyprosta-5-cis,13-trans-dienoic acid methyl ester are dissolved in a mixture of 2 ml. of benzene and 3 ml. of acetone containing 5 mg. of freshly prepared tris-(triphenylphosphine)chlororhodium, at room temperature. The resulting mixture is stirred in a hydrogen atmosphere and aliquots are removed at periodic intervals. The aliquots are analyzed by gas liquid chromatography to determine whether hydrogenation has been completed. When the hydrogenation is determined to be essentially complete (ca. 6 hours) the reaction mixture is applied to 20% wt. silver nitrate impregnated silica gel (G) preparative plates developing with chloroform:methanol:acetic acid:water in a 95:75:1:0.6 parts by volume ratio. The zone corresponding to the desired monounsaturated compound is eluted with a 90:10, by vol., of a mixture of chloroform and methanol yielding the pure 8R-11α-hydroxymethyl-9β,15α-dihydroxyprost-13-trans-enoic acid methyl ester (V, $R^{4\prime}$ = Me).

Similarly starting from the corresponding 11α-hydroxymethylprosta-5-cis,13-trans-dienoic acid derivatives obtained in Examples 3, 8 and 9 there are obtained the following compounds:

8R-11α-hydroxymethyl-9α,15α-dihydroxyprost-13-trans-enoic acid methyl ester,
11α-hydroxymethyl-9α,15α-dihydroxyprost-13-trans-enoic acid methyl ester,
11α-hydroxymethyl-9β,15α-dihydroxyprost-13-trans-enoic acid methyl ester,
8R-9-keto-11α-hydroxymethyl-15α-hydroxyprost-13-trans-enoic acid methyl ester, and
9-keto-11α-hydroxymethyl-15α-hydroxyprost-13-trans-enoic acid methyl ester.

Upon hydrolysis of the methyl ester group, in accordance with the method of Example 10, there are obtained the respective free acids, namely:

8R-11α-hydroxymethyl-9β,15α-dihydroxyprost-13-trans-enoic acid,
8R-11α-hydroxymethyl-9α,15α-dihydroxyprost-13-trans-enoic acid,
11α-hydroxymethyl-9β,15α-dihydroxyprost-13-trans-enoic acid,
11α-hydroxymethyl-9α,15α-dihydroxyprost-13-trans-enoic acid,
8R-9-keto-11α-hydroxymethyl-15α-hydroxyprost-13-trans-enoic acid and
9-keto-11α-hydroxymethyl-15α-hydroxyprost-13-trans-enoic acid.

EXAMPLE 12

By following the hydrogenation method of Example 11, 20 mg. of 8R-9-keto-11α-acetoxymethyl-15α-acetoxyprosta-5-cis,13-trans-dienoic acid methyl ester is converted into 8R-9-keto-11α-acetoxymethyl-15α-acetoxyprost-13-trans-enoic acid methyl ester.

To a solution of 15 mg. of 8R-9-keto-11α-acetoxymethyl-15α-acetoxyprost-13-trans-enoic acid methyl ester in 2 ml. of methanol is added a solution of 60 mg. of potassium carbonate in 1 ml. of water, under nitrogen atmosphere, and the reaction mixture is kept at room temperature for 20 hours. It is then acidified to pH-2 with 1% hydrochloric acid solution and extracted several times with ethyl acetate. The combined organic extracts are washed with saturated sodium chloride solution, dried over sodium sulfate and evaporated to dryness under reduced pressure. Purification of the residue by thin layer chromatography affords 8R-9-keto-11α-hydroxymethyl-15α-hydroxyprost-13-trans-enoic acid (8R-antimer of XI, $R^{4\prime}$ = H) in pure form, identical to the product obtained in Example 11.

EXAMPLE 13

A. A mixture of 50 mg. of 8R-11α-hydroxymethyl-9β,15α-dihydroxyprosta-5-cis,13-trans-dienoic acid methyl ester, 2 ml. of dioxane and 100 mg. of 2,3-dichloro-5,6-dicyano-1,4-benzoquinone is stirred at 50° to 55°C for 18 hours. The reaction mixture is then evaporated to dryness under reduced pressure and the residue is dissolved in methylene chloride and chromatographed on Florisil. The fractions eluted with methylene chloride-ether (9:1) afford 8R-9β-hydroxy-11α-hydroxymethyl-15-ketoprosta-5-cis,13-trans-dienoic acid methyl ester in pure form (8R-antimer of XIII, Z = double bond).

B. To a solution of 100 mg. of 8R-11α-hydroxymethyl-9β,15α-dihydroxyprosta-5-cis,13-trans-dienoic acid methyl ester in 5 ml. of anhydrous tetrahydrofuran are added 400 mg. of activated manganese dioxide, and the reaction mixture is stirred at room temperature for 6 hours. The manganese dioxide is then filtered off and washed with acetone and the combined filtrates are evaporated to dryness under reduced pressure. The residue is redissolved in tetrahydrofuran and stirred with another 400 mg. batch of manganese dioxide as above, repeating the operation twice. After final evaporation of the solvent and purification of the residue by chromatography on Florisil there is obtained the pure 8R-9β-hydroxy-11α-hydroxymethyl-15-ketoprosta-5-cis,13-trans-dienoic acid methyl ester, identical to the compound obtained in part A.

By the above-described methods, starting from the corresponding 8R-antimeric or racemic prostadienoic or prostenoic acid methyl ester compounds there are obtained:

8-R-9α-hydroxy-11α-hydroxymethyl-15-ketoprosta-5-cis,13-trans-dienoic acid methyl ester, 8R-9α-hydroxy-11α-hydroxymethyl-15-ketoprost-13-trans-enoic acid methyl ester, 8R-9β-hydroxy-11α-hydroxymethyl-15-ketoprost-13-trans-enoic acid methyl ester, 9α-hydroxy-11α-hydroxymethyl-15-ketoprosta-5-cis,13-trans-dienoic acid methyl ester, 9β-hydroxy-11α-hydroxymethyl-15-ketoprosta-5-cis,13-trans-dienoic acid methyl ester, 9α-hydroxy-11α-hydroxymethyl-15-ketoprost-13-trans-enoic acid methyl ester and 9β-hydroxy-11α-hydroxymethyl-15-ketoprost-13-trans-enoic acid methyl ester.

EXAMPLE 14

A solution of 228 mg. of 8R-9β-hydroxy-11α-hydroxymethyl-15-ketoprosta-5-cis,13-trans-dienoic acid methyl ester in 20 ml. of anhydrous ether is cooled to −20°C and treated dropwise, under stirring and under argon atmosphere with 6 molar equivalents of a 3N methylmagnesium bromide solution in ether. The temperature of the reaction mixture is allowed to rise to −5°C., 6 additional molar equivalents of methylmagnesium bromide solution are added, and the resulting mixture is stirred for 1 hour more, at the end of which time there are added 5 ml. of methanol. The resulting mixture is diluted with water and ethyl acetate, and the insoluble material filtered through Celite, diatomaceous earth. The organic phase is separated from the filtrate and washed with saturated sodium chloride solution, dried over magnesium sulfate and evaporated to dryness under reduced pressure. The oily residue is purified by thin layer chromatography, to produce the pure 8R-11α-hydroxymethyl-15β-methyl-9β,15α-dihydroxyprosta-5-cis,13-trans-dienoic acid methyl ester and 8R-11α-hydroxymethyl-15α-methyl-9β,15β-dihydroxyprosta-5-cis,13-trans-dienoic acid methyl ester in approximately equal amounts [8R-antimers of XIV (R³ and R⁴ʹ = Me; Z = double bond)].

In a similar manner but using ethylmagnesium bromide in place of methylmagnesium bromide there are obtained 8R-11α-hydroxymethyl-15β-ethyl-9β,15α-dihydroxyprosta-5-cis,13-trans-dienoic acid methyl ester and the 15α-ethyl-15β-hydroxy isomer.

EXAMPLE 15

To 280 mg. of 8R-9β-hydroxy-11α-hydroxymethyl-15-ketoprosta-5-cis,13-trans-dienoic acid methyl ester are added 6 ml. of a (1:1) mixture of N-trimethylsilyl-diethylamine and anhydrous acetone, and the reaction mixture is kept at room temperature, under argon atmosphere, for 6 hours. The reaction mixture is then evaporated to dryness under reduced pressure and the oily residue is dissolved in 10 ml. of anhydrous tetrahydrofuran. The resulting solution is cooled to −20°C and treated dropwise, under argon atmosphere, with 6 molar equivalents of 3N methylmagnesium bromide in ether, maintaining the temperature below −5°C; 6 additional molar equivalents of the Grignard reagent are added and the reaction mixture stirred at −5°C for 1 hour further, diluted with saturated ammonium chloride solution and extracted with ether. The organic extract is washed with saturated sodium chloride solution, dried over magnesium sulfate and evaporated to dryness under vacuo. The residue is dissolved in 10 ml. of 70% aqueous methanol and treated with 0.1 ml. of a mixture of acetic acid-water (0.2:3), maintaining the reaction mixture at room temperature for 18 hours. It is then evaporated to dryness under vacuo and the residue purified by thin layer chromatography to yield 8R-11α-hydroxymethyl-15β-methyl-9β,15α-dihydroxyprosta-5-cis,13-trans-dienoic acid methyl ester and the 15α-methyl-15β-hydroxy isomer, identical to the products obtained in Example 14.

EXAMPLE 16

By following the method of Examples 14 or 15, the remaining 15-keto compounds obtained in Example 13 are converted into the corresponding 15 ξ -methyl-15 ξ -hydroxy derivatives, namely:

8R-11α-hydroxymethyl-15 ξ -methyl-9α,15 ξ -dihydroxyprosta-5-cis,13-trans-dienoic acid methyl ester, 8R-11α-hydroxymethyl-15 ξ -methyl-9α,15 ξ -dihydroxyprost-13-trans-enoic acid methyl ester, 8R-11α-hydroxymethyl-15 ξ -methyl-9β,15 ξ -dihydroxyprost-13-trans-enoic acid methyl ester, 11α-hydroxymethyl-15 ξ -methyl-9α,15 ξ -dihydroxyprosta-5-cis-13-trans-dienoic acid methyl ester, 11α-hydroxymethyl-15 ξ -methyl-9β,15 ξ -dihydroxyprosta-5-cis,13-trans-dienoic acid methyl ester, 11α-hydroxymethyl-15 ξ -methyl-9α,15 ξ -dihydroxyprost-13-trans-enoic acid methyl ester, and 11α-hydroxymethyl-15 ξ -methyl-9α,15 ξ -dihydroxyprost-13-trans-enoic acid methyl ester, separating the 15α-hydroxy-15β-methyl and 15β-hydroxy-15α-methyl isomers by thin layer chromatography.

Likewise but using ethylmagnesium bromide in place of methylmagnesium bromide as alkylating agent, the corresponding 15α-hydroxy-15β-ethyl and 15β-hydroxy-15α-ethyl analogs of the above-mentioned compounds are produced.

EXAMPLE 17

A mixture of 250 mg. of 8R-11α-hydroxymethyl-15β-methyl-9β,15α-dihydroxyprosta-5-cis,13-trans-dienoic acid methyl ester, 1 ml. of pyridine and 75 mg. of acetic anhydride is kept at 0°–5°C for 3 hours. It is then evaporated to dryness under vacuo, and the oily residue taken up in ethyl acetate. The resulting solution is washed several times with 50% saturated sodium chloride solution, dried and evaporated to dryness.

Purification of the residue by t.l.c. affords the pure 8R-11α-acetoxymethyl-15β-methyl-9β,15α-dihydroxyprosta-5-cis,13-trans-dienoic acid methyl ester (8R-antimer of XV, $R^3$ = Me, Z = double bond).

EXAMPLE 18

To a suspension of 2 g. of Celite, diatomaceous earth (dried for 24 hours at 105°C) and 1 g. of chromium trioxide-dipyridine complex, [prepared as described by J. C. Collins et al., in *Tetrahedron Letters*, 3363 (1968)] in 15 ml. of methylene chloride, cooled to −5°C is added, with stirring, a solution of 130 mg. of 8R-11α-acetoxymethyl-15β-methyl-9β,15α-dihydroxyprosta-5-cis,13-trans-dienoic acid methyl ester in 5 ml. of methylene chloride and the mixture is stirred for 15 minutes further at 0°–5°C; 300 mg. of sodium bisulfate monohydrate are then added and the reaction mixture is stirred for an additional 10 minute period. The insoluble material is separated by filtration and washed well with methylene chloride. The combined organic filtrate are evaporated to dryness under vacuo and the residue purified by thin layer chromatography, thus obtaining 8R-9-keto-11α-acetoxymethyl-15β-methyl-15α-hydroxyprosta-5-cis, 13-trans-dienoic acid methyl ester (8R-antimer of XVI, $R^3$ = Me; Z = double bond) in pure form.

EXAMPLE 19

To a solution of 50 mg. of 8R-9-keto-11α-acetoxymethyl-15β-methyl-15α-hydroxyprosta-5-cis,13-trans-dienoic acid methyl ester in 2 ml. of anhydrous methanol is added under nitrogen atmosphere, 17.3 mg. (1.1 molar equivalents) of anhydrous potassium carbonate and the reaction mixture is stirred at room temperature for 90 minutes. It is then poured into water and extracted with ethyl acetate. The combined organic extracts are washed with saturated sodium chloride solution, dried over sodium sulfate and evaporated to dryness under vacuo. The oily residue is purified by t.l.c., to afford 8R-9-keto-11α-hydroxymethyl-15β-methyl-15α-hydroxyprosta-5-cis,13-trans-dienoic acid methyl ester (8R-antimer of XVII, $R^3$ and $R^{4'}$ = Me; Z = double bond) in pure form.

EXAMPLE 20

Examples 17, 18 and 19 are repeated using the following compounds as starting materials:
8R-11α-hydroxymethyl-15β-ethyl-9β,15α-dihydroxyprosta-5-cis,13-trans-dienoic acid methyl ester,
8R-11α-hydroxymethyl-15α-methyl-9α,15β-dihydroxyprosta-5-cis,13-trans-dienoic acid methyl ester,
8R-11α-hydroxymethyl-15β-methyl-9β,15α-dihydroxyprost-13-trans-enoic acid methyl ester,
8R-11α-hydroxymethyl-15α-ethyl-9α,15β-dihydroxyprost-13-trans-enoic acid methyl ester,
11α-hydroxymethyl-15β-methyl-9α,15α-dihydroxyprosta-5-cis-13-trans-dienoic acid methyl ester,
11α-hydroxymethyl-15β-methyl-9β,15α-dihydroxyprost-13-trans-enoic acid methyl ester, and
11α-hydroxymethyl-15β-ethyl-9β,15α-dihydroxyprost-13-trans-enoic acid methyl ester,
there are produced respectively as final products:
8R-9-keto-11α-hydroxymethyl-15β-ethyl-15α-hydroxyprosta-5-cis,13-trans-dienoic acid methyl ester,
8R-9-keto-11α-hydroxymethyl-15α-methyl-15β-hydroxyprosta-5-cis,13-trans-dienoic acid methyl ester,
8R-9-keto-11α-hydroxymethyl-15β-methyl-15α-hydroxyprost-13-trans-enoic acid methyl ester,
8R-9-keto-11α-hydroxymethyl-15α-ethyl-15β-hydroxyprost-13-trans-enoic acid methyl ester,
9-keto-11α-hydroxymethyl-15β-methyl-15α-hydroxyprosta-5-cis,13-trans-dienoic acid methyl ester,
9-keto-11α-hydroxymethyl-15β-methyl-15β-hydroxyprost-13-trans-enoic acid methyl ester, and
9-keto-11α-hydroxymethyl-15β-ethyl-15α-hydroxyprost-13-trans-enoic acid methyl ester.

EXAMPLE 21

To a solution of 110 mg. of 8R-9-keto-11α-hydroxymethyl-15β-methyl-15α-hydroxyprosta-5-cis,13-trans-dienoic acid methyl ester in 2.2 ml. of methanol are added 165 mg. of potassium carbonate and 0.66 ml. of water, under nitrogen atmosphere, and the reaction mixture is kept at room temperature for 16 hours. It is then evaporated to dryness and the oily residue taken up in 10 ml. of water and 10 ml. of methylene chloride. The aqueous phase is separated and the organic phase which contains the unsaponifiable products is washed with saturated sodium potassium tartrate solution. The combined aqueous phases are saturated with sodium potassium tartrate, cooled to −10°C and treated dropwise with 23.9 ml. of a 0.1N solution of acetic acid. It is then extracted three times with cold ethyl acetate and the combined organic extracts washed with saturated sodium potassium tartrate solution, dried and evaporated to dryness. The residue is purified by t.l.c., to afford the pure 8R-9-keto-11α-hydroxymethyl-15β-methyl-15α-hydroxyprosta-5-cis,13-trans-dienoic acid (8R-antimer of XVII, $R^3$ = Me; $R^{4'}$ = H; Z = double bond).

EXAMPLE 22

A. A suspension of 4 g. of crude pancreatic lipase (Sigma L-3126) in 40 ml. of a 0.1 M sodium chloride and 0.05 M calcium chloride solution in water is stirred at 25°C for 1 hour. The mixture is then centrifuged for 1 hour at 5000 rev./min. and at 25° to 30°C. The supernatant is neutralized with 1N sodium hydroxide solution to pH 7.2 to 7.4 and used directly for the hydrolysis of the prostaglandin derivatives of the invention.

B. Forty-two milligrams of 8R-11α-hydroxymethyl-15β-methyl-9α,15α-dihydroxyprosta-5-cis,13-trans-dienoic acid methyl ester are dissolved by sonication at 37°C for 20 minutes in 30 ml. of the lipase solution prepared as described in part A. The reaction mixture is magnetically stirred for 24 hours at 25° to 26°C, adjusting constantly the pH at 7.2 to 7.4 during the reaction period with 0.1N sodium hydroxide solution. The cold reaction mixture is then acidified with 0.1N acetic acid solution and the product extracted several times from the solution with ethyl acetate and ether. The combined organic extracts are dried over sodium sulfate and evaporated to dryness under vacuo. The residue is dissolved in methylenechloride and chromatographed on 3 g. of Florisil. The column is eluted successively with methylene chloride-diethyl ether mixtures, diethyl ether, diethyl ether-ethyl acetate mixtures, pure ethyl acetate and ethyl acetate containing 1% methanol. The fractions eluted with the latter solvent mixture afford the pure 8R-11α-hydroxymethyl-15β-methyl-9α,15α-dihydroxyprosta-5-cis,13-trans-dienoic acid (8R antimer of XIV, $R^3$=Me; $R^{4'}$=H; Z=double bond).

Similarly by following the above procedure, 8R-9-keto-11α-hydroxymethyl-15β-methyl-15α-hydroxyprosta-5-cis-13-trans-dienoic acid methyl ester is converted into 8R-9-keto-11α-hydroxymethyl-15β-methyl-15α-hydroxyprosta-5-cis,13-trans-dienoic acid, identical to the product obtained in Example 21.

EXAMPLE 23

To a solution of 400 mg. of 8R-9-keto-11α-hydroxymethyl-15α-hydroxyprosta-5-cis,13-trans-dienoic acid methyl ester in 3 ml. of methanol is added a solution of 400 mg. of hydroxylamine hydrochloride and 500 mg. of sodium acetate in 10 ml. of methanol-water (1:1). The resulting reaction mixture is kept at room temperature for 18 hours under argon atmosphere and the solvent is then eliminated under reduced pressure. The residue is taken up in water and the mixture extracted with ethyl acetate, the organic phase is separated, washed with saturated sodium chloride solution, dried over magnesium sulfate and evaporated to dryness under vacuo, thus obtaining 9-hydroxyimino-11α-hydroxymethyl-15α-hydroxyprosta-5-cis,13-trans-dienoic acid methyl ester. (8R-antimer of XIX, Z=double bond).

EXAMPLE 24

A mixture of 100 mg. of 8R-9-hydroxyimino-11α-hydroxymethyl-15α-hydroxyprosta-5-cis,13-trans-dienoic acid methyl ester, 5 ml. of dioxane and 200 mg. of 2,3-dichloro-5,6-dicyano-1,4-benzoquinone is stirred at 50° to 55°C for 18 hours. The solvent is then eliminated under reduced pressure and the residue purified by t.l.c., to afford 8R-9-hydroxyimino-11α-hydroxymethyl-15-ketoprosta-5-cis,13-trans-dienoic acid methyl ester (8R-antimer of XX, Z=double bond) in pure form.

EXAMPLE 25

A. To a stirred mixture of 1.5 ml. of hexamethyldisilazane and 0.3 ml. of trimethylchlorosilane there is added a solution of 100 mg. of 8R-9-hydroxyimino-11α-hydroxymethyl-15-keto-prosta-5-cis,13-trans-dienoic acid methyl ester in 8 ml. of anhydrous tetrahydrofuran, under an argon atmosphere and the resulting mixture is stirred at room temperature, under anhydrous conditions for 16 hours. It is then evaporated to dryness under reduced pressure. The residue is dissolved in 5 ml. of toluene and the solvent eliminated under vacuo, repeating the operation several times, thus obtaining the crude 8R-9-trimethylsilyloxyimino-11α-trimethylsilyloxymethyl-15-ketoprosta-5-cis,13-trans-dienoic acid methyl ester (8R antimer of XXI, Z=double bond).

B. The foregoing crude product is dissolved in 10 ml. of anhydrous diethyl ether, and the resulting solution is cooled to −78°C in a dry ice-acetone bath. To the stirred cold solution is added dropwise an ether solution of 1.1 molar equivalents of methyllithium (1.3 ml. of 0.22M methyllithium in ether) under stirring and under an argon atmosphere. The resulting stirred mixture is allowed to attain room temperature, and stirred 2 additional hours at this temperature. It is then poured into saturated ammonium chloride solution, the ethereal phase is separated, washed with saturated sodium chloride solution, dried over magnesium sulfate and evaporated to dryness under vacuo, thus obtaining the crude 8R-9-trimethylsilyloxyimino-11α-trimethylsilyloxymethyl-15 § -methyl-15 § -hydroxyprosta-5-cis,13-trans-dienoic acid methyl ester. (8R-antimers of XXII; $R^3$ = Me; Z=double bond).

C. A solution of 50 mg. of the crude 8R-9-trimethylsilyloxyimino-11α-trimethylsilyloxymethyl-15 § -hydroxy-15 § -methylprosta-5-cis,13-trans-dienoic acid methyl ester in 5 ml. of 70% aqueous methanol containing 0.05 ml. of a 0.2:3 mixture of acetic acid-water is keppt at room temperature for 18 hours. The reaction mixture is then evaporated to dryness under reduced pressure and the residue purified by thin layer chromatography using ethyl acetate-ether (75:25) as eluant, thus obtaining the individual isomers, i.e., 8R-9-hydroxyimino-11α-hydroxymethyl-15β-methyl-15α-hydroxyprosta-5-cis,13-trans-dienoic acid methyl ester and 8R-9-hydroxyimino-11α-hydroxymethyl-15α-methyl-15β-hydroxyprosta-5-cis,13-trans-dienoic acid methyl ester in pure form.

D. To a stirred solution of 150 mg. of 8R-9-hydroxyimino-11α-hydroxymethyl-15β-methyl-15α-hydroxyprosta-5-cis,13-trans-dienoic acid methyl ester in 3 ml. of methanol is added a solution of 150 mg. of thallium (III) nitrate in 3 ml. of methanol. The reaction mixture is stirred at room temperature for 10 minutes, and the formed precipitate separated by filtration ans washed with methanol. The filtrate is cooled to 0°C, and acidified with dilute acetic acid, stirring the mixture for 5 minutes. It is then extracted with ether and the organic extract washed with saturated sodium chloride solution, dried over magnesium sulfate and evaporated to dryness under reduced pressure. The residue is purified by chromatography on Florisil. The fractions eluted with diethyl ether-ethyl acetate (9:1) afford the pure 8R-9-keto-11α-hydroxymethyl-15β-methyl-15α-hydroxyprosta-5-cis,13-trans-dienoic acid methyl ester, identical to the compound obtained in Example 19.

EXAMPLE 26

A mixture of 90 mg. of 8R-11α-hydroxymethyl-15β-methyl-9α,15α-dihydroxyprosta-5-cis,13-trans-dienoic acid methyl ester, 1.8 g. of dry finely ground freshly extracted residue of the gorgonian *Plexaura homomalla* (Esper), [which results after extraction of the prostaglandin derivatives contained originally by this gorgonian, as described by A. Prince et al., in *Prostaglandins*, Vol. 3, No. 4, p. 531 (1973)] and 10 ml. of a 0.1M sodium chloride and 0.05M calcium chloride solution in water is stirred at room temperature for 24 hours, maintaining the pH of the reaction mixture at 7.5–7.7 by addition of 0.1N sodium hydroxide solution. At the end of this time the reaction mixture is diluted with 15 ml. of acetone, adjusting the pH to 4, with dilute acetic acid. Charcoal is added to decolorize the solution, and the insoluble material separated by filtration through Celite, diatomaceous earth, washing the solids with several portions of acetone. The combined filtrates are concentrated under reduced pressure to a small volume, and the product extracted from the aqueous residue with methylene chloride. The combined organic extracts are dried over magnesium sulfate and evaporated to dryness under reduced pressure. The oily residue is purified by t.l.c., thus obtaining the pure 8R-11α-hydroxymethyl-15β-methyl-9α,15α-dihydroxyprosta-5-cis,13-trans-dienoic acid, identical to the compound obtained in Example 22.

Likewise, 8R-11α-hydroxymethyl-9α,15α-dihydroxyprosta-5-cis,13-trans-dienoic acid, and 8R-11α-hydroxymethyl-9β,15α-dihydroxyprosta-5-cis,13-trans-dienoic acid, as well as the corresponding racemic compounds are obtained, starting from the methyl ester derivatives thereof.

EXAMPLE 27

By following the hydrolysis methods of Examples 21, 22 or 26, the other 8R-antimeric of racemic 15-alkylated-15-hydroxy prostadienoic and prostenoic acid methyl ester derivatives obtained in Examples 14, 16 and 20 are converted into the corresponding free acids, e.g., 8R-11α-hydroxymethyl-15β-methyl-9β,15α-dihydroxyprosta-5-cis,13-trans-dienoic acid, 8R-11α-hydroxymethyl-15β-ethyl-9β,15α-dihydroxyprosta-5-cis,13-trans-dienoic acid, 8R-11α-hydroxymethyl-15β-methyl-9α,15α-dihydroxyprost-13-trans-enoic acid, 8R-11α-hydroxymethyl-15β-methyl-9β,15α-dihydroxyprost-13-trans-enoic acid, 11α-hydroxymethyl-15β-methyl-9α,15α-dihydroxyprosta-5-cis-13-trans-dienoic acid, 11α-hydroxymethyl-15β-methyl-9β,15α-dihydroxyprosta-5-cis-13-trans-dienoic acid, 11α-hydroxymethyl-15β-ethyl-9β,15α-dihydroxyprosta-5-cis-13-trans-dienoic acid, 11α-hydroxymethyl-15β-methyl-9α,15α-dihydroxyprost-13-trans-enoic acid, 11α-hydroxymethyl-15β-methyl-9β,15α-dihydroxyprost-13-trans-enoic acid, 8R-9-keto-11α-hydroxymethyl-15β-ethyl-15α-hydroxyprosta-5-cis-13,trans-dienoic acid, 8R-9-keto-11α-hydroxymethyl-15β-methyl-15α-hydroxyprost-13-trans-enoic acid, 9-keto-11α-hydroxymethyl-15β-methyl-15α-hydroxyprosta-5-cis-13-trans-dienoic acid, and 9-keto-11α-hydroxymethyl-15β-methyl-15α-hydroxyprost-13-trans-enoic acid, as well as the corresponding 15α-alkyl-15β-hydroxy isomers.

EXAMPLE 28

To a solution of 100 mg. of 8R-9-keto-11α-hydroxymethyl-15β-methyl-15α-hydroxyprosta-5-cis,13-trans-dienoic acid in 5 ml. of ether is added 1 ml. of an ethereal solution of diazoethane, and the reaction mixture is maintained at room temperature for 10 minutes. The solvents and excess reagent are eliminated by vacuum distillation and the residue is purified by t.l.c. to afford 8R-9-keto-11α-hydroxymethyl-15β-methyl-15α-hydroxyprosta-5-cis,13-trans-dienoic acid ethyl ester.

In a similar manner but using diazopropane in place of diazoethane, the propyl ester of 8R-9-keto-11α-hydroxymethyl-15β-methyl-15α-hydroxyprosta-5-cis,13-trans-dienoic acid is obtained.

By the same method, 8R-9-keto-11α-hydroxymethyl-15β-methyl-15α-hydroxyprost-13-trans-enoic acid, 8R-11α-hydroxymethyl-15β-methyl-9β,15α-dihydroxyprosta-5-cis,13-trans-dienoic acid, 8R-11α-hydroxymethyl-15β-ethyl-9α,15α-dihydroxyprosta-5-cis-13-trans-dienoic acid, 9-keto-11α-hydroxymethyl-15β-ethyl-15α-hydroxyprosta-5-cis-13-trans-dienoic acid and 11α-hydroxymethyl-15β-methyl-9β,15α-dihydroxyprost-13-trans-enoic acid, are converted into the corresponding ethyl and propyl esters.

EXAMPLE 29

A mixture of 50 mg. of 8R-11α-hydroxymethyl-15β-methyl-9β,15α-dihydroxyprosta-5-cis,13-trans-dienoic acid, 0.4 ml. of pyridine and 1.0 ml. of acetic anhydride is kept at room temperature for 1 hour. The reaction mixture is then evaporated to dryness under reduced pressure and the residue is dissolved in ethyl acetate, 50 mg. of sodium bisulfate are added and the solution is filtered through Celite, diatomaceous earth. The filtrate is evaporated to dryness under vacuo to yield 8R-9β-acetoxy-11α-acetoxymethyl-15β-methyl-15α-hydroxyprosta-5-cis,13-trans-dienoic acid.

Similarly but using propionic, caproic and valeric anhydrides as esterifying agents there are respectively obtained:

8R-9β-propionoxy-11α-propionoxymethyl-15β-methyl-15α-hydroxyprosta-5-cis,13-trans-dienoic acid, 8R-9β-caproxy-11α-caproxymethyl-15β-methyl-15α-hydroxyprosta-5-cis,13-trans-dienoic acid and 8R-9β-valeroxy-11α-valeroxymethyl-15β-methyl-15α-hydroxyprosta-5-cis,13-trans-dienoic acid.

Likewise, starting from 8R-9-keto-11α-hydroxymethyl-15β-methyl-15α-hydroxyprosta-5-cis,13-trans-dienoic acid methyl ester there are produced:

8R-9-keto-11α-acetoxymethyl-15β-methyl-15α-hydroxyprosta-5-cis,13-trans-dienoic acid methyl ester, 8R-9-keto-11α-propionoxymethyl-15β-methyl-15α-hydroxyprosta-5-cis,13-trans-dienoic acid methyl ester, 8R-9-keto-11α-caproxymethyl-15β-methyl-15α-hydroxyprosta-5-cis,13-trans-dienoic acid methyl ester and 8R-9-keto-11α-valeroxymethyl-15β-methyl-15α-hydroxyprosta-5-cis,13-trans-dienoic acid methyl ester, respectively.

By the same method but using 8R-11α-hydroxymethyl-15β-methyl-9α,15α-dihydroxyprosta-5-cis,13-trans-dienoic acid methyl ester, 8R-11α-hydroxymethyl-15β-ethyl-9β,15α-dihydroxyprost-13-trans-enoic acid methyl ester and 9-keto-11α-hydroxymethyl-15β-methyl-15α-hydroxyprost-13-trans-enoic acid as starting materials and acetic anhydride as esterifying agent, there are obtained respectively:

8R-9α-acetoxy-11α-acetoxymethyl-15β-methyl-15α-hydroxyprosta-5-cis,13-trans-dienoic acid methyl ester, 8R-9β-acetoxy-11α-acetoxymethyl-15β-ethyl-15α-hydroxyprost-13-trans-enoic acid methyl ester and 9-keto-11α-acetoxymethyl-15β-methyl-15α-hydroxyprost-13-trans-enoic acid.

EXAMPLE 30

To a solution of 100 mg. of 8R-9-keto-11α-hydroxymethyl-15β-methyl-15α-hydroxyprosta-5-cis,13-trans-dienoic acid in 10 ml. of methanol is added 3.0 ml. of a 0.1N solution of sodium hydroxide, and the mixture is stirred at room temperature for 1 hour. It is then evaporated to dryness under reduced pressure, to give the sodium salt of 8R-9-keto-11α-hydroxymethyl-15β-methyl-15α-hydroxyprosta-5-cis,13-trans-dienoic acid.

By employing 1.1 molar equivalents of potassium hydroxide (in the form of a 0.1N solution) in place of sodium hydroxide in the above procedure the potassium salt of 8R-9-keto-11α-hydroxymethyl-15β-methyl-15α-hydroxyprosta-5-cis,13-trans-dienoic acid is obtained.

Similarly, the sodium and potassium salts of the other 15-alkylated prostadienoic and prostenoic acid derivatives obtained in Examples 22, 26 and 27 are produced.

EXAMPLE 31

To a solution of 100 mg. of 8R-11α-hydroxymethyl-15β-methyl-9β,15α-dihydroxyprosta-5-cis,13-trans-dienoic acid in 10 ml. of methanol is added a mixture of 3 ml. of concentrated ammonium hydroxide solution and 5 ml. of methanol. The resulting mixture is stirred for 2 hours at room temperature and then evaporated to dryness, to yield the ammonium salt of 8R-11α-hydroxymethyl-15β-methyl-9β,15α-dihydroxyprosta-5-cis-13-trans-dienoic acid.

By employing dimethylamine, diethylamine or dipropylamine in place of ammonium hydroxide in the above process the corresponding salts of 8R-11α-hydroxymethyl-15β-methyl-9β,15α-dihydroxyprosta-5-cis,13-trans-dienoic acid are obtained.

In a similar manner, the ammonium, dimethylamine, diethylamine and dipropylamine salts of the other 15-alkylated prostadienoic and prostenoic acid derivatives of the previous Examples can be prepared.

EXAMPLE 32

To a mixture of 142 mg. of procaine and 5 ml. of aqueous methanol is added 100 mg. of 8R-9-keto-11α-hydroxymethyl-15β-methyl-15α-hydroxyprosta-5-cis,13-trans-dienoic acid in 5 ml. of methanol and the resultant reaction mixture is stirred at room temperature for 16 hours. It is then evaporated to dryness under reduced pressure to give the procaine salt of 8R-9-keto-11α-hydroxymethyl-15β-methyl-15α-hydroxyprosta-5-cis,13-trans-dienoic acid.

Similarly, the lysine, caffeine and arginine salts thereof are obtained. In like manner, the procaine, lysine, caffeine and arginine salts of the other 15-methyl(ethyl)prostadienoic and prostenoic acid derivatives obtained in Examples 22, 26 and 27 can be produced e.g., the procaine salt of 8R-11α-hydroxymethyl-15β-methyl-9α,15α-dihydroxyprosta-5-cis,13-trans-dienoic acid, the caffeine salt of 8R-9-keto-11α-hydroxymethyl-15β-ethyl-15α-hydroxyprosta-5-cis,13-trans-dienoic acid, the lysine salt of 8R-11α-hydroxymethyl-15β-methyl-9β,15α-dihydroxyprost-13-trans-enoic acid and the arginine salt of 8R-9-keto-11α-hydroxymethyl-15β-methyl-15α-hydroxyprost-13-trans-enoic acid, as well as the corresponding salts of the racemic compounds.

What is claimed is:

1. An 8R-antimeric or racemic compound selected from the group of those represented by the following formula:

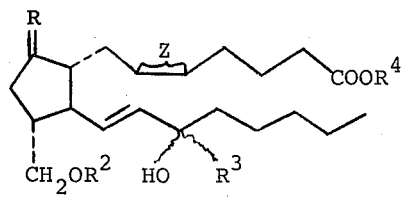

wherein
R is the grouping

each of $R^1$ and $R^2$ is hydrogen or a hydrocarbon carboxylic group of 1 to 6 carbon atoms;
$R^3$ is methyl or ethyl;
$R^4$ is hydrogen, a lower alkyl group of 1 to 6 carbon atoms or the pharmaceutically acceptable, non-toxic salts of compounds in which $R^4$ is hydrogen;
Z is a cis double bond and the wavy lines ( $\wr$ ) indicate the α or β configuration or mixtures thereof, provided that when $R^3$ is α, the hydroxyl group, attached to the same carbon atom as $R^3$, is β; and when $R^3$ is β, the hydroxyl group, attached to the same carbon atom as $R^3$, is α.

2. A compound according to claim 1 wherein R is α-hydroxy-β-hydrogen and $R^2$ and $R^4$ are hydrogen.

3. A compound according to claim 1 wherein R is β-hydroxy-α-hydrogen and $R^2$ and $R^4$ are hydrogen.

4. A compound according to claim 1 wherein $R^2$ and $R^4$ are hydrogen.

5. A compound according to claim 1 wherein $R^3$ is methyl and $R^2$ and $R^4$ are hydrogen.

6. A compound according to claim 1 wherein said compound is an 8R-antimer.

7. A compound according to claim 6 wherein R is α-hydroxy-β-hydrogen, $R^2$ and $R^4$ are hydrogen, $R^3$ is β-methyl and Z is a cis-double bond, 8R-11α-hydroxymethyl-15β-methyl-9α,15α-dihydroxyprosta-5-cis,13-trans-dienoic acid and the non-toxic, pharmaceutically acceptable salts thereof.

8. A compound according to claim 6 wherein R is α-hydroxy-β-hydrogen, $R^2$ is hydrogen, $R^3$ is β-methyl, $R^4$ is methyl and Z is a cis-double bond, 8R-11α-hydroxymethyl-15β-methyl-9α,15α-dihydroxyprosta-5-cis,13-trans-dienoic acid methyl ester.

9. A compound according to claim 6 wherein R is β-hydroxy-α-hydrogen, $R^2$ and $R^4$ are hydrogen, $R^3$ is β-methyl and Z is a cis double bond, 8R-11α-hydroxymethyl-15β-methyl-9β,15α-dihydroxyprosta-5-cis,13-trans-dienoic acid and the non-toxic, pharmaceutically acceptable salts thereof.

10. A compound according to claim 6 wherein R is β-hydroxy-α-hydrogen, $R^2$ is hydrogen, $R^3$ is β-methyl, $R^4$ is methyl and Z is a cis double bond, 8R-11α-hydroxymethyl-15β-methyl-9β,15α-dihydroxyprosta-5-cis,13-trans-dienoic acid methyl ester.

11. A compound according to claim 1 wherein said compound is a racemic compound.

12. A compound according to claim 11 wherein R is α-hydroxy-β-hydrogen, $R^2$ and $R^4$ are hydrogen, $R^3$ is methyl and Z is a cis-double bond, 11α-hydroxymethyl-15 $\wr$ -methyl-9α,15 $\wr$ -dihydroxyprosta-5-cis,13-trans-dienoic acid and the nontoxic, pharmaceutically acceptable salts thereof.

13. A compound according to claim 11 wherein R is α-hydroxy-β-hydrogen, $R^2$ is hydrogen, $R^3$ and $R^4$ are methyl and Z is a cis-double bond, 11α-hydroxymethyl-15 $\wr$ -methyl-9α,15 $\wr$ -dihydroxyprosta-5-cis,13-trans-dienoic acid methyl ester.

14. A compound according to claim 11 wherein R is β-hydroxy-α-hydrogen, $R^2$ and $R^4$ are hydrogen, $R^3$ is methyl and Z is a cis double bond, 11α-hydroxymethyl-15 $\wr$ -methyl-9β,15 $\wr$ -dihydroxyprosta-5-cis,13-trans-dienoic acid and the nontoxic, pharmaceutically acceptable salts thereof.

15. A compound according to claim 11, wherein R is β-hydroxy-α-hydrogen, R² is hydrogen, R³ and R⁴ are methyl and Z is a cis double bond, 11α-hydroxymethyl-15ξ-methyl-9β,15ξ-dihydroxyprosta-5-cis,13-trans-dienoic acid methyl ester.

* * * * *